(12) United States Patent
McIntyre et al.

(10) Patent No.: US 6,602,872 B1
(45) Date of Patent: Aug. 5, 2003

(54) SUBSTITUTED PYRIDAZINES HAVING CYTOKINE INHIBITORY ACTIVITY

(75) Inventors: Charles J. McIntyre, Lansdale, PA (US); Nigel J. Liverton, Harleysville, PA (US); David A. Claremon, Maple Glen, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/717,277

(22) Filed: Nov. 21, 2000

Related U.S. Application Data

(60) Provisional application No. 60/170,319, filed on Dec. 13, 1999.

(51) Int. Cl.[7] .................... C07D 403/04; C07D 403/14; A61K 31/506; A61K 31/5377; A61P 19/10

(52) U.S. Cl. .................. 514/252.02; 544/238; 544/122; 544/60; 540/601; 540/575; 514/252.03

(58) Field of Search .......................... 544/238, 60, 122; 514/252.02, 252.03; 540/575, 601

(56) References Cited

FOREIGN PATENT DOCUMENTS

| | | |
|---|---|---|
| WO | WO 99 32448 | 7/1999 |

OTHER PUBLICATIONS

Opal et al (Infectious Disease Clinics of North America 13(2), pp. 285–297, Jun. 1999).*

Chaby (Drug Discovery Today 4(5) 209–221, May 1999).*

Anon., "Septic Shock", http://www.copewithcytokines.de/cope.cgi?005493.*

BioWorld Today, vol. 9, No. 59, Mar. 30, 1998.*

\* cited by examiner

*Primary Examiner*—Mark L. Berch
*Assistant Examiner*—Kahsay Habte
(74) *Attorney, Agent, or Firm*—Mitul I. Desai; David L. Rose

(57) ABSTRACT

There are disclosed compounds of formula (I)

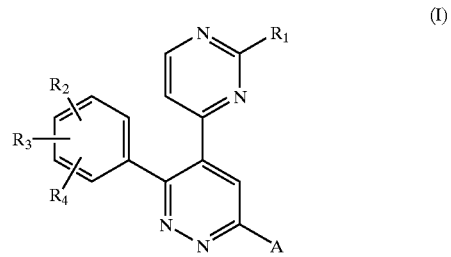

and pharmaceutically acceptable salts thereof which exhibit utility for the treatment of cytokine mediated diseases such as arthritis.

9 Claims, No Drawings

SUBSTITUTED PYRIDAZINES HAVING CYTOKINE INHIBITORY ACTIVITY

This application claims the benefit of U.S. Provisional Application Ser. No. 60/170,319, filed Dec. 13, 1999.

BACKGROUND OF THE INVENTION

The present invention relates to substituted pyridazine compounds which have cytokine inhibitory activity. Cytokine mediated diseases and cytokine inhibition, suppression and antagonism are used in the context of diseases or conditions in which excessive or unregulated production or activity of one or more cytokines occurs. Examples of cytokines which are effected typically include Interleukin-1 (IL-1), Interleukin-6 (IL-6), Interleukin-8 (IL-8) and Tumor Necrosis Factor (TNF).

Interleukin-1 (IL-1) and Tumor Necrosis Factor (TNF) are produced by a variety of cells that are involved in immunoregulation and other physiological conditions.

There are many disease states in which IL-1 is implicated. Examples are rheumatoid arthritis, osteoarthritis, endotoxemia, toxic shock syndrome, acute and chronic inflammatory diseases, such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis and acute synovitis. Recent evidence also links IL-1 activity to diabetes.

Interleukin-1 has been demonstrated to mediate a variety of biological activities thought to be important in immunoregulation and other physiological conditions. [See, e.g., Dinarello et al., Rev. Infect. Disease, 6, 51 (1984)]. The known biological activities of IL-1 include the activation of T helper cells, induction of fever, stimulation of prostaglandin or collagenase production, neutrophil chemotaxis, induction of acute phase proteins and the suppression of plasma iron levels.

Excessive or unregulated tumor necrosis factor (TNF) production or activity has been implicated in mediating or exacerbating rheumatoid arthritis, rheumatoid spondylitis, osteoarthritis, gouty arthritis, and other arthritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcosis, bone resorption diseases, reperfusion injury, graft v. host rejection, allograft rejections, fever and myalgia due to infection, cachexia secondary to infection or malignancy, cachexia secondary to acquired immune deficiency syndrome (AIDS), AIDS related complex (ARC), keloid formation, scar tissue formation, Crohn's disease, ulcerative colitis and pyresis.

Monokines, such as TNF, have also been shown to activate HIV replication in monocytes and/or macrophages [See Poli, et al., Proc. Natl. Acad. Sci., 87:782–784 (1990)], therefore, inhibition of monokine production or activity aids in limiting HIV progression. TNF has been implicated in various roles with other viral infections, such as the cytomegalovirus (CMV), influenza virus and the herpes virus.

Interleukin-6 (IL-6) is a cytokine effecting the immune system and hematopoiesis. It is produced by several mammalian cell types in response to agents such as IL-1, and is correlated with disease states such as angiofollicular lymphoid hyperplasia.

Interleukin-8 (L-8) is a chemotactic factor first identified and characterized in 1987. Many different names have been applied to IL-8, such as neutrophil attractant/activation protein-1 (NAP-1), monocyte derived neutrophil chemotactic factor (MDNCF), neutrophil activating factor (NAF), and T-cell lymphocyte chemotactic factor. Like IL-1, IL-8 is produced by several cell types, including mononuclear cells, fibroblasts, endothelial cells and ketainocytes. Its production is induced by IL-1, TNF and by lipopolysaccharide (LPS). IL-8 stimulates a number of cellular functions in vitro. It is a chemoattractant for neutrophils, T-lymphocytes and basophils. It induces histamine release from basophils. It causes lysozomal enzyme release and respiratory burst from neutrophils, and it has been shown to increase the surface expression of Mac-1 (CD 11b/CD 18) on neutrophils without de novo protein synthesis.

There remains a need for compounds which are useful in treating cytokine mediated diseases, and as such, inhibit, suppress or antagonize the production or activity of cytokines such as IL-1, IL-6, IL-8 and TNF.

SUMMARY OF THE INVENTION

The present invention relates to compound I of the formula

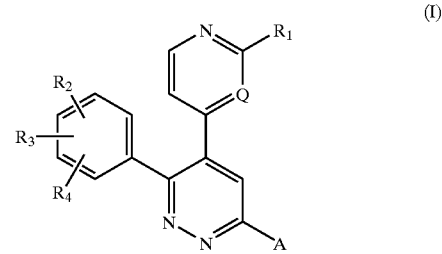

wherein

A is halogen, phenyl, S(O)$_m$ phenyl, or NR$_5$R$_6$;

R$_1$ is hydrogen, NH(C$_1$–C$_6$ alkyl)aryl, NH(C$_1$–C$_6$ alkyl) or NH(C$_3$–C$_6$ cycloalkyl), said aryl group being optionally substituted by 1–3 groups selected from halogen, hydroxy, CF$_3$, NH$_2$, and NO$_2$;

R$_2$, R$_3$ and R$_4$ independently represent a member selected from the group consisting of hydrogen, halogen, hydroxy, CF$_3$, NH$_2$, NO$_2$, C$_1$–C$_6$ alkyl, C$_1$–C$_6$ alkoxy, C$_3$–C$_8$ cycloalkyl or phenyl;

R$_5$ and R$_6$ are independently hydrogen, C$_1$–C$_6$ alkyl, (C$_1$–C$_6$ alkyl)—O—(C$_1$–C$_6$ alkyl), (C$_1$–C$_6$ alkyl) cycloalkyl, (C$_1$–C$_6$ alkyl) NR$_7$R$_8$, C$_1$–C$_6$ alkylphenyl, said phenyl group optionally substituted with 1 to 3 groups selected from (C$_1$–C$_6$ alkyl) or (C$_1$–C$_6$ alkoxy); (C$_1$–C$_6$ alkyl)—NHCOO—(C$_1$–C$_6$ alkyl), (C$_1$–C$_6$ alkyl)C≡C, (C$_1$–C$_6$ alkyl)indole, (C$_1$–C$_6$ alkyl) pyridinyl, a pyrrolidinyl or piperidyl group, said groups optionally substituted with C$_1$–C$_6$ alkyl or benzyl; or R$_5$ and R$_6$ are taken together with the nitrogen atom to form an optionally substituted 4 to 10 membered mono, bicyclic or azabicyclic heterocyclic ring containing at least one N atom, and optionally containing 1–2 additional N atoms and 0–2 O or S atoms, said ring optionally substituted by 1–3 groups selected from C$_1$–C$_6$alkyl, OH, O(C$_1$–C$_6$ alkyl), COO(C$_1$–C$_6$ alkyl), C$_1$–C$_6$alkyl benzodioxole, CONR$_7$R$_8$, phenyl, said phenyl group optionally substituted with halogen, C$_1$–C$_6$alkyl, C$_1$–C$_6$ alkoxy; CH(aryl)$_2$ said aryl optionally substituted with 1–3 groups selected from C$_1$–C$_6$alkyl, OH or halogen; NR$_7$R$_8$ or a pipefidino or a pyrrolidino group;

R₇ and R₈ are independently hydrogen, $C_1-C_6$ alkyl, $(C_1-C_6$ alkyl)—O—$(C_1-C_6$ alkyl), $C_1-C_6$ alkylaryl, $(C_1-C_6$ alkyl)—NHCOO—$(C_1-C_6$ alkyl), COO—$(C_1-C_6$ alkyl), a pyrrolidinyl or piperidyl group, said groups optionally substituted with $C_1-C_6$ alkyl or $C_1-C_6$ alkylaryl; or R₇ and R₈ are taken together with the nitrogen atom to form an optionally substituted 4 to 10 membered mono, bicyclic or azabicyclic heterocyclic ring containing at least one N atom, and optionally containing 1–2 additional N atoms and 0–1 O or S atoms, said ring optionally substituted by 1–3 groups selected from $C_1-C_4$ alkyl, OH, O($C_1-C_6$ alkyl), Q is CH or N;

m is 0,1 or 2;

or a pharmaceutically acceptable addition salt and/or hydrate thereof, or where applicable, a geometric or optical isomer or racemic mixture thereof.

This invention also relates to a pharmaceutical composition that is comprised of a compound of formula I as defined above in combination with a pharmaceutically acceptable carrier.

Also included in the invention is a method of treating a cytokine mediated disease in a mammal, comprising administering to a mammalian patient in need of such treatment an amount of a compound of formula I which is effective for treating said cytokine mediated disease.

DETAILED DESCRIPTION OF THE INVENTION

The present invention relates to compound I of the formula

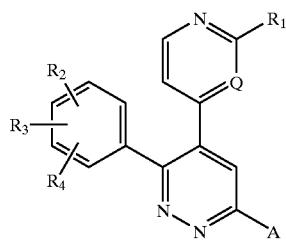

(I)

wherein

A is halogen, phenyl, $S(O)_m$ phenyl, or $NR_5R_6$;

R₁ is hydrogen, NH($C_1-C_6$ alkyl)aryl, NH($C_1-C_6$ alkyl) or NH($C_3-C_6$ cycloalkyl), said aryl group being optionally substituted by 1–3 groups selected from halogen, hydroxy, $CF_3$, $NH_2$, and $NO_2$;

R₂, R₃ and R₄ independently represent a member selected from the group consisting of hydrogen, halogen, hydroxy, $CF_3$, $NH_2$, $NO_2$, $C_1-C_6$ alkyl, $C_1-C_6$ alkoxy, $C_3-C_8$ cycloalkyl or phenyl;

R₅ and R₆ are independently hydrogen, $C_1-C_6$ alkyl, $(C_1-C_6$ alkyl)—O—$(C_1-C_6$ alkyl), $(C_1-C_6$ alkyl) cycloalkyl, $(C_1-C_6$ alkyl) $NR_7R_8$, $C_1$–C6 alkylphenyl, said phenyl group optionally substituted with 1 to 3 groups selected from $(C_1-C_6$ alkyl) or $(C_1-C_6$ alkoxy); $(C_1-C_6$ alkyl)—NHCOO—$(C_1-C_6$ alkyl), $(C_1-C_6$ alkyl)C≡C, $(C_1-C_6$ alkyl)indole, $(C_1-C_6$ alkyl) pyridinyl, a pyrrolidinyl or piperidyl group, said groups optionally substituted with $C_1-C_6$ alkyl or benzyl; or R₅ and R₆ are taken together with the nitrogen atom to form an optionally substituted 4 to 10 membered mono, bicyclic or azabicyclic heterocyclic ring containing at least one N atom, and optionally containing 1–2 additional N atoms and 0–2 O or S atoms, said ring optionally substituted by 1–3 groups selected from $C_1-C_6$ alkyl, OH, O($C_1-C_6$ alkyl), COO($C_1-C_6$ alkyl), $C_1-C_6$ alkyl benzodioxole, $CONR_7R_8$, phenyl, said phenyl group optionally substituted with halogen, $C_1-C_6$ alkyl, $C_1-C_6$ alkoxy; CH(aryl)₂ said aryl optionally substituted with 1–3 groups selected from $C_1-C_6$ alkyl, OH or halogen; $NR_7R_8$ or a piperidino or a pyrrolidino group;

R₇ and R₈ are independently hydrogen, $C_1-C_6$ alkyl, $(C_1-C_6$ alkyl)—O—$(C_1-C_6$ alkyl), $C_1-C_6$ alkylaryl, $(C_1-C_6$ alkyl)—NHCOO—$(C_1-C_6$ alkyl), COO—$(C_1-C_6$ alkyl), a pyrrolidinyl or pipenidyl group, said groups optionally substituted with $C_1-C_6$ alkyl or $C_1-C_6$ alkylaryl; or R₇ and R₈ are taken together with the nitrogen atom to form an optionally substituted 4 to 10 membered mono, bicyclic or azabicyclic heterocyclic ring containing at least one N atom, and optionally containing 1–2 additional N atoms and 0–1 O or S atoms, said ring optionally substituted by 1–3 groups selected from $C_1-C_4$ alkyl, OH, O($C_1-C_6$ alkyl), Q is CH or N;

m is 0, 1 or 2;

or a pharmaceutically acceptable addition salt and/or hydrate thereof, or where applicable, a geometric or optical isomer or racemic mixture thereof.

This invention also relates to a pharmaceutical composition that is comprised of a compound of formula I as defined above in combination with a pharmaceutically acceptable carrier.

Also included in the invention is a method of treating a cytokine mediated disease in a mammal, comprising administering to a mammalian patient in need of such treatment an amount of a compound of formula I which is effective for treating said cytokine mediated disease.

In a preferred embodiment, there is disclosed a compound of the formula

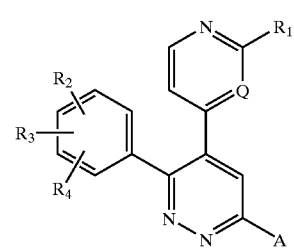

(I)

wherein

A is $NR_5R_6$;

R₁ is NH($C_1-C_6$ alkyl)aryl, said aryl group being optionally substituted by 1–3 groups selected from halogen, hydroxy, $CF_3$, $NH_2$, and $NO_2$;

R₂ is $CF_3$;

Q is N;

or a pharmaceutically acceptable addition salt and/or hydrate thereof, or where applicable, a geometric or optical isomer or racemic mixture thereof.

Representative species falling within the present invention include the following:

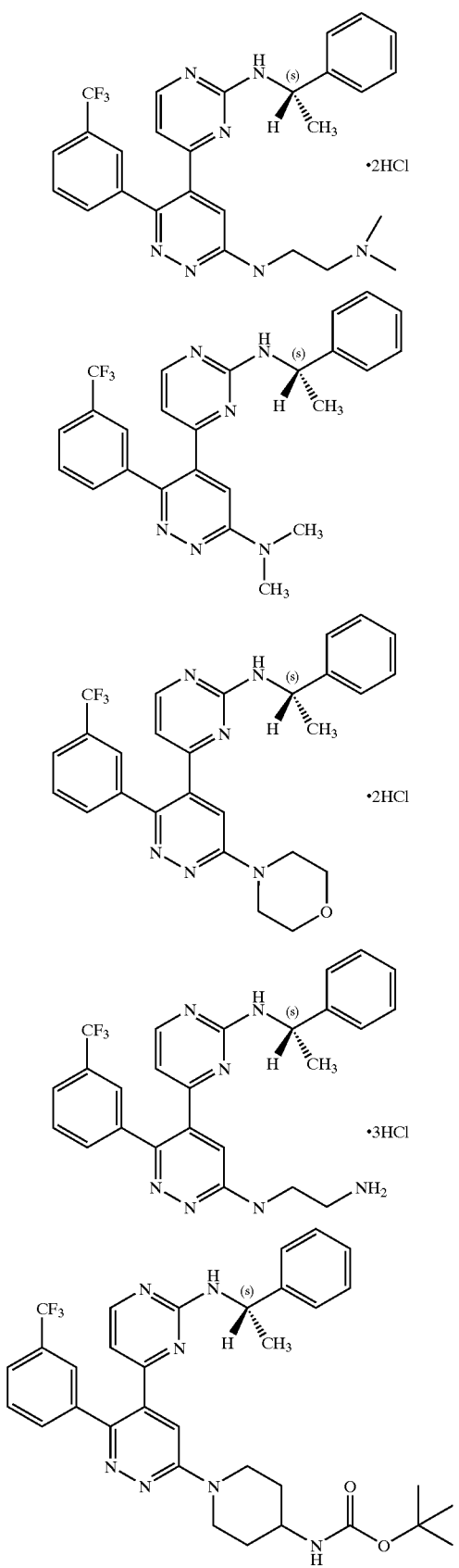
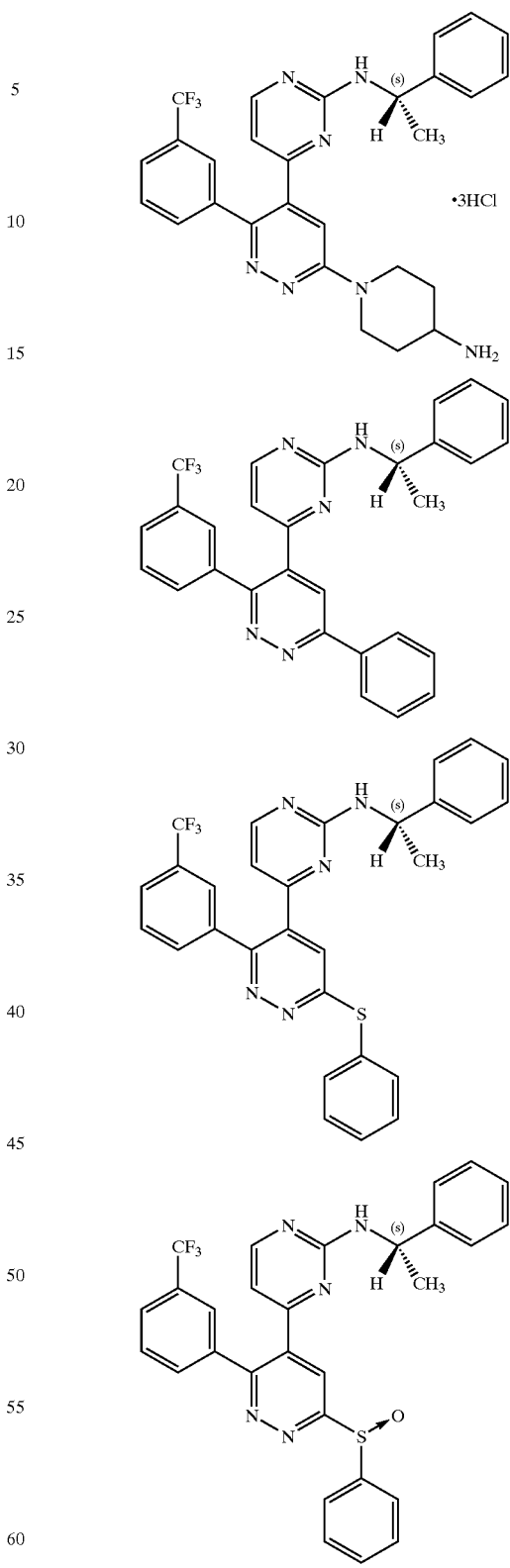
Other representative compounds of the invention include primary and secondary amines wherein A is as shown in the table below:

TABLE 1
Reaction of 10 With 1° or 2° Amines
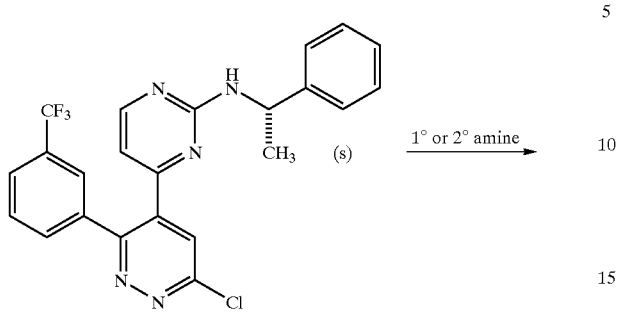
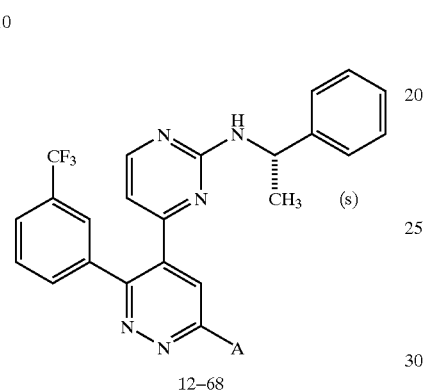
| Number | A |
|---|---|
| 12 | 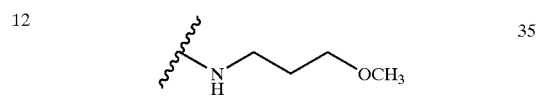 |
| 13 | 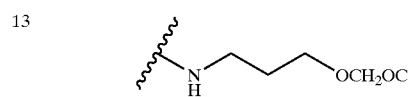 |
| 14 | 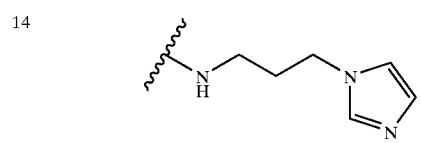 |
| 15 | 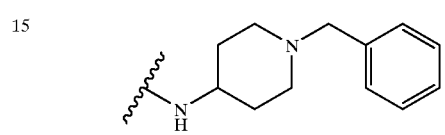 |
| 16 | 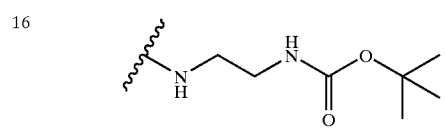 |
| 17 | 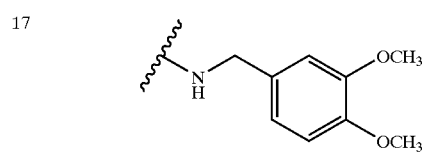 |
TABLE 1-continued
| | |
|---|---|
| 18 | 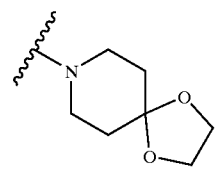 |
| 19 | 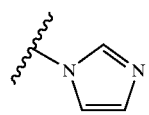 |
| 20 | 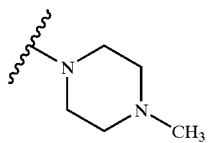 |
| 21 | 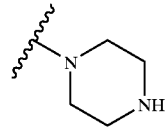 |
| 22 | 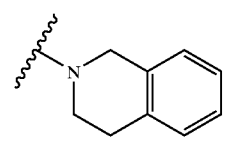 |
| 23 | 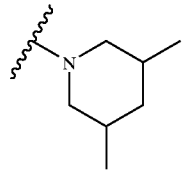 |
| 24 | 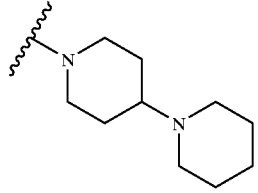 |
| 25 | 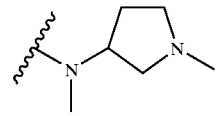 |
| 26 | 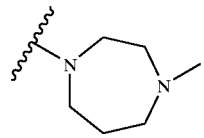 |

TABLE 1-continued
| | |
|---|---|
| 27 | 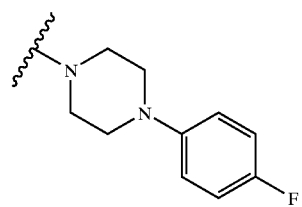 |
| 28 | 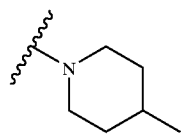 |
| 29 | 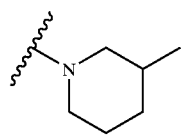 |
| 30 | 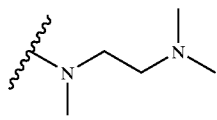 |
| 31 | 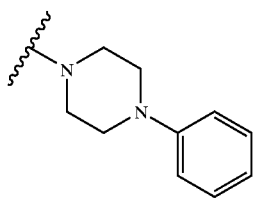 |
| 32 | 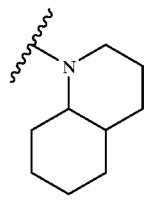 |
| 33 | 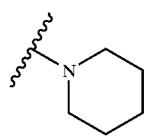 |
| 34 | 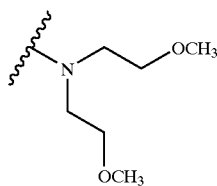 |
| 35 | 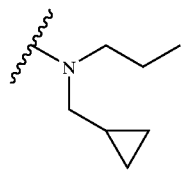 |
| 36 | 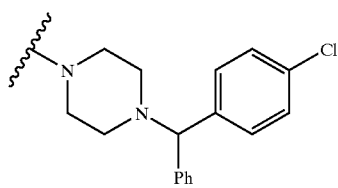 |
| 37 | 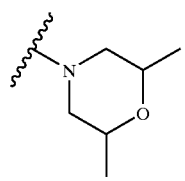 |
| 38 | 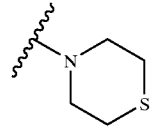 |
| 39 | 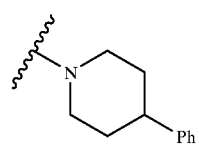 |
| 40 | 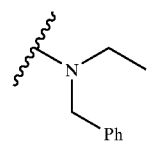 |
| 41 | 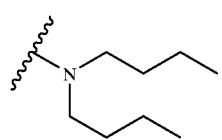 |
| 42 | 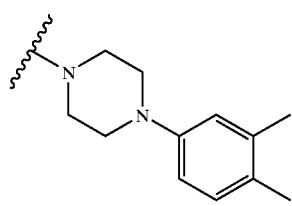 |
| 43 | 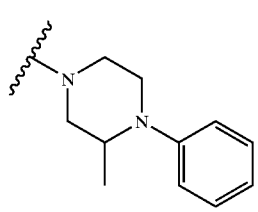 |

TABLE 1-continued
| | | | | |
|---|---|---|---|---|
| 44 | 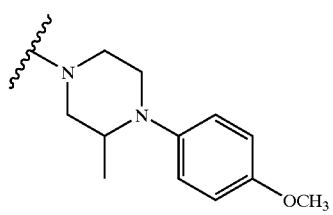 | | 54 | 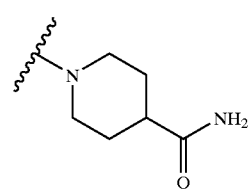 |
| 45 | 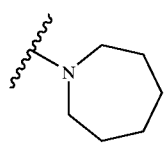 | | 55 | 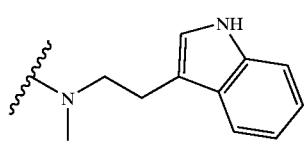 |
| 46 | 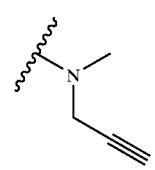 | | 56 | 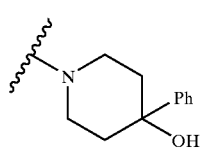 |
| 47 | 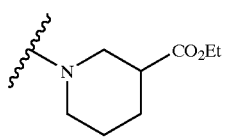 | | 57 | 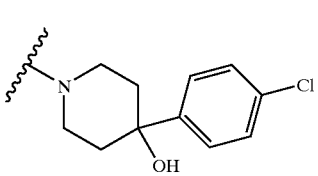 |
| 48 | 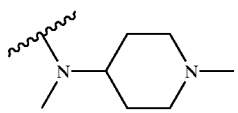 | | 58 | 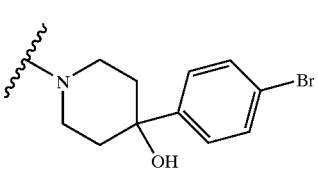 |
| 49 | 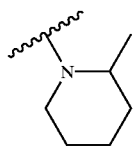 | | 59 | 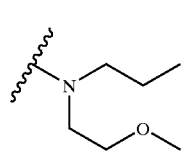 |
| 50 | 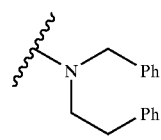 | | 60 | 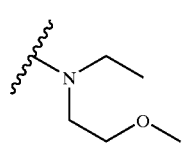 |
| 51 | 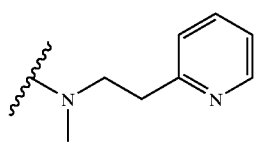 | | 61 | 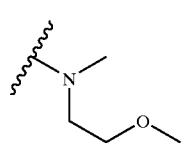 |
| 52 | 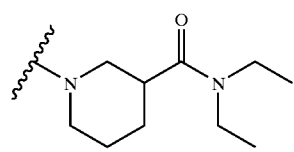 | | 62 | 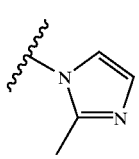 |
| 53 | 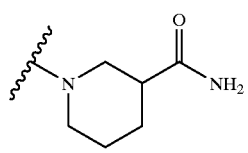 | | | |

TABLE 1-continued

| | |
|---|---|
| 63 | 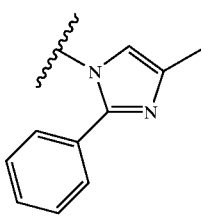 |
| 64 | 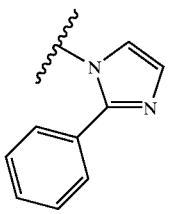 |
| 65 | 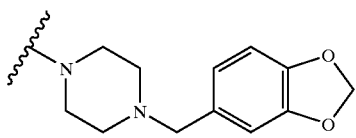 |
| 66 | 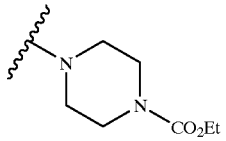 |
| 67 | 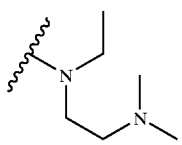 |
| 68 | 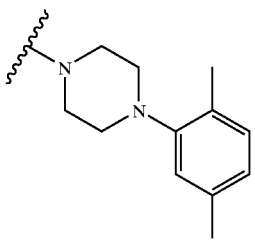 |

Unless otherwise stated or indicated, the following definitions shall apply throughout the specification claims.

The term "alkyl" refers to a monovalent alkane (hydrocarbon) derived radical containing from 1 to 15 carbon atoms unless otherwise defined. It may be straight or branched, and when of sufficient size, e.g., $C_{3-15}$, may be cyclic. Preferred straight or branched alkyl groups include methyl, ethyl, propyl, isopropyl, butyl and t-butyl. Preferred cycloalkyl groups include cyclopropyl, cyclopentyl and cyclohexyl.

Alkyl also includes an alkyl group substituted with a cycloalkyl group, such as cyclopropylmethyl. Alkyl also includes a straight or branched alkyl group.

The alkylene and monovalent alkyl portion(s) of the alkyl group can be attached at any available point of attachment to the cycloalkylene portion.

When substituted alkyl is present, this refers to a straight, branched or cyclic alkyl group as defined above, substituted with 1–3 groups as defined with respect to each variable.

The term "aryl" refers to aromatic rings e.g., phenyl, substituted phenyl and like groups as well as rings which are fused, e.g., naphthyl and the like. Aryl thus contains at least one ring having at least 6 atoms, with up to two such rings being present, containing up to 10 atoms therein, with alternating (resonating) double bonds between adjacent carbon atoms. The preferred aryl groups are phenyl and naphthyl. Aryl groups may likewise be substituted as defined below. Preferred substituted aryls include phenyl or naphthyl substituted with one or two groups.

The terms "heterocycloalkyl" and "heterocyclyl" refer to a cycloalkyl group (nonaromatic) in which one of the carbon atoms in the ring is replaced by a heteroatom selected from O, $S(O)_m$ or N, and in which up to three additional carbon atoms may be replaced by said heteroatoms. When three heteroatoms are present in the heterocycle, they are not all linked together.

Examples of heterocyclyls are piperidinyl, morpholinyl, azetidinyl, pyrrolidinyl, tetrahydrofuranyl, imidazolinyl, piperazinyl, pyrolidin-2-one, piperidin-2-one and the like.

The term "halogen" or "halo" is intended to include fluorine, chlorine, bromine and iodine.

As used herein, the term "composition" is intended to encompass a product comprising the specified ingredients in the specified amounts, as well as any product which results, directly or indirectly, from combination of the specified ingredients in the specified amounts.

In addition, it is well known to those skilled in the art that many of the foregoing heterocyclic groups can exist in more than one tautomeric form. It is intended that all such tautomers be included within the ambit of this invention.

The optical isomeric forms, that is mixtures of enantiomers, e.g., racemates, or diastereomers as well as individual enantiomers or diastereomers of the instant compound are included. These individual enantiomers are commonly designated according to the optical rotation they effect by the symbols (+) and (−), (L) and (D), (l) and (d) or combinations thereof. These isomers may also be designated according to their absolute spatial configuration by (S) and (R), which stands for sinister and rectus, respectively.

The individual optical isomers may be prepared using conventional resolution procedures, e.g., treatment with an appropriate optically active acid, separating the diastereomers and then recovering the desired isomer. In addition, the individual optical isomers may be prepared by asymmetric synthesis.

Additionally, a given chemical formula or name shall encompass pharmaceutically acceptable addition salts thereof and solvates thereof, such as hydrates.

The compounds of the present invention, while effective themselves, may be formulated and administered in the form of their pharmaceutically acceptable addition salts for purposes of stability, convenience of crystallization, increased solubility and other desirable properties.

The compounds of the present invention may be administered in the form of pharmaceutically acceptable salts. The term "pharmaceutically acceptable salt" is intended to include all acceptable salts. Examples of acid salts are hydro-chloric, nitric, sulfuric, phosphoric, formic, acetic, trifluoroacetic, propionic, maleic, succinic, malonic, methane sulfonic and the like which can be used as a dosage form for modifying the solubility or hydrolysis characteristics or can be used in sustained release or prodrug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris (hydroxymethyl) amino-methane, and tetramethylammonium hydroxide. These salts may be prepared by standard procedures, e.g. by reacting a free acid with a suitable organic or inorganic base, or alternatively by reacting a free base with a suitable organic or inorganic acid.

Also, in the case of an acid (—COOH) or alcohol group being present, pharmaceutically acceptable esters can be employed, e.g. methyl, ethyl, butyl, acetate, maleate, pivaloyloxymethyl, and the like, and those esters known in the art for modifying solubility or hydrolysis characteristics for use as sustained release or prodrug formulations.

The compounds of the present invention may have chiral centers other than those centers whose stereochemistry is depicted in formula I, and therefore may occur as racemates, racemic mixtures and as individual enantiomers or diastereomers, with all such isomeric forms being included in the present invention as well as mixtures thereof. Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

The term "TNF mediated disease or disease state" refers to disease states in which TNF plays a role, either by production or increased activity levels of TNF itself, or by causing another cytokine to be released, such as but not limited to IL-1 or IL-6. A disease state in which IL-1, for instance is a major component, and whose production or action, is exacerbated or secreted in response to TNF, would therefore be considered a disease state mediated by TNF.

The term "cytokine" as used herein means any secreted polypeptide that affects the functions of cells and is a molecule which modulates interactions between cells in the immune, inflammatory or hematopoietic response. A cytokine includes, but is not limited to, monokines and lymphokines regardless of which cells produce them. Examples of cytokines include, but are not limited to, Interleukin-1 (IL-1), Interleukin-6 (IL-6), Interleukin-8 (IL-8), Tumor Necrosis Factor-alpha (TNF-α) and Tumor Necrosis Factor-beta (TNF-β).

By the term "cytokine interfering or cytokine suppresive amount" is meant an effective amount of a compound of formula I which will cause a decrease in the in vivo activity or level of the cytokine to normal or sub-normal levels, when given to the patient for the prophylaxis or therapeutic treatment of a disease state which is exacerbated by, or caused by, excessive or unregulated cytokine production or activity.

The compounds of the invention are prepared by the following reaction scheme(s). All substituents are as defined above unless indicated otherwise.

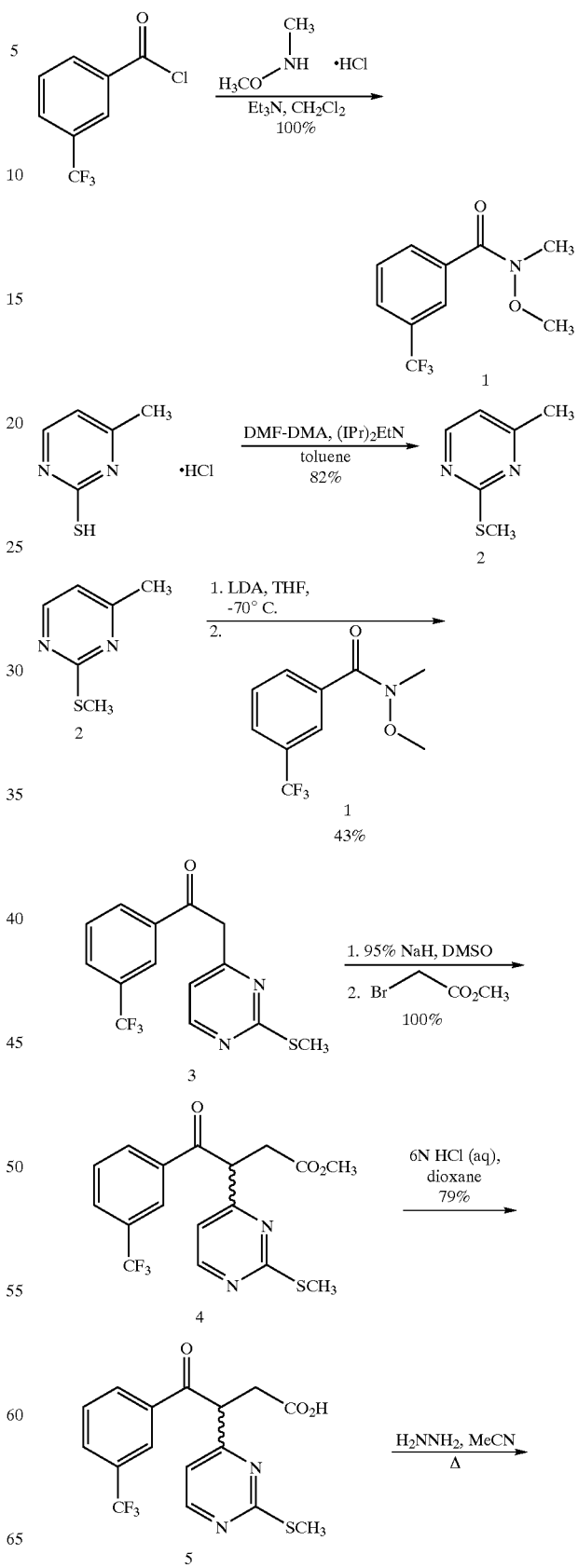

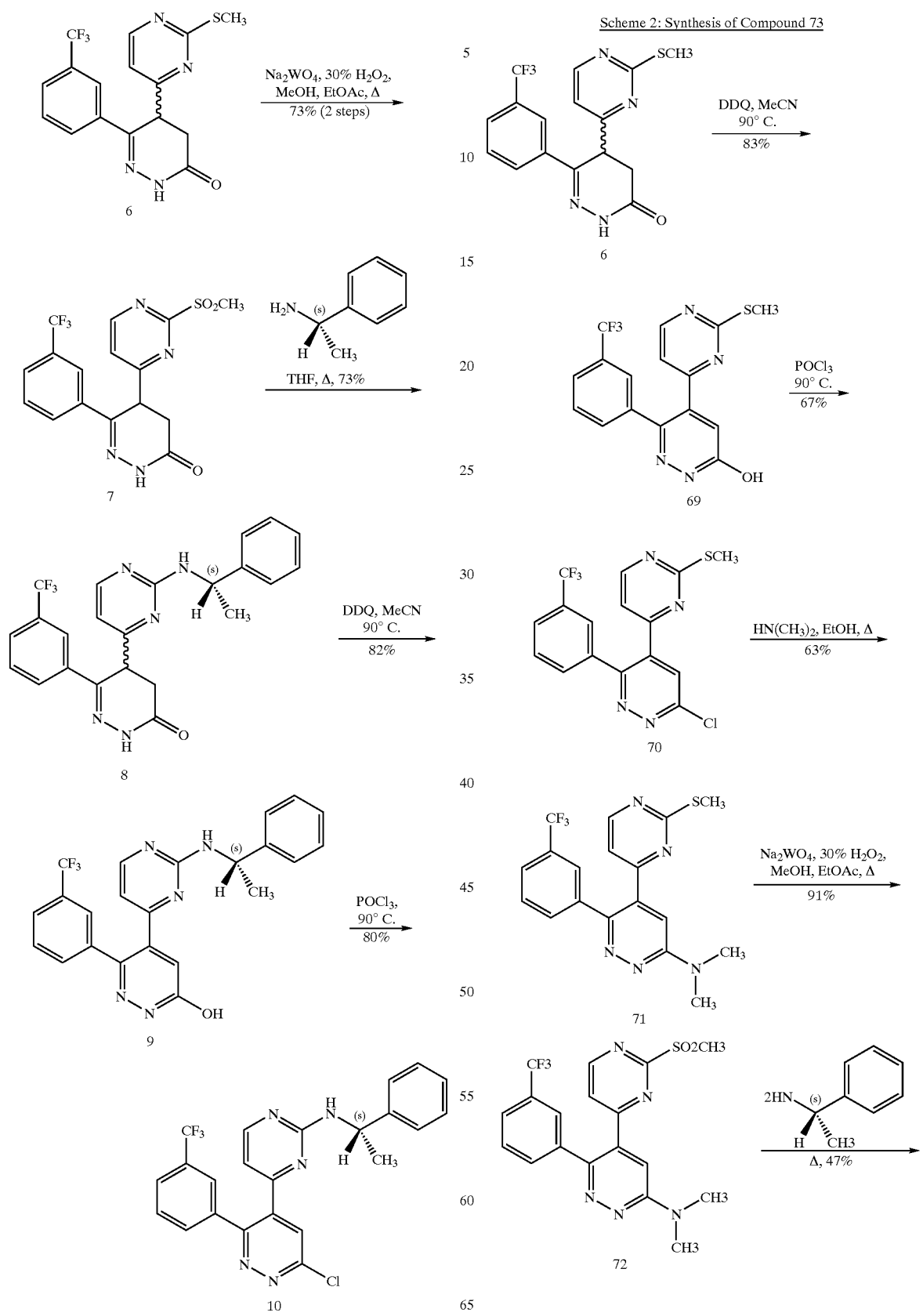

-continued
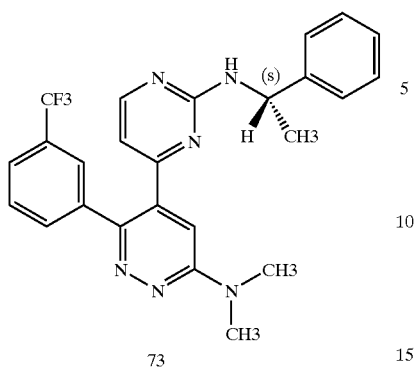
73
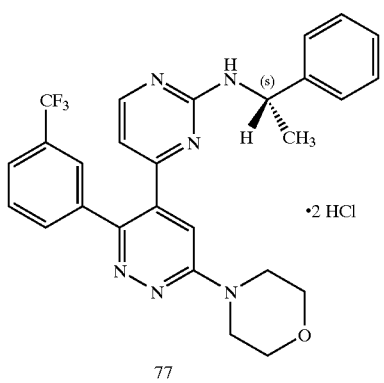
77
Scheme 3: Synthesis of Compound 77
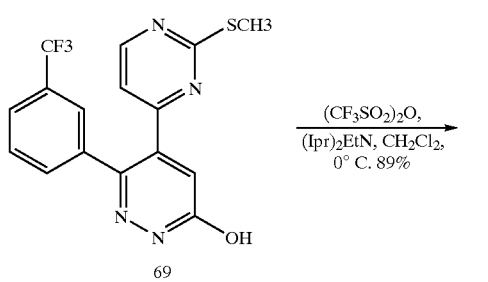
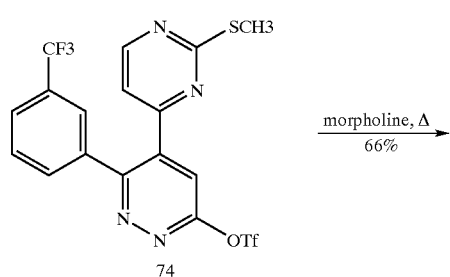
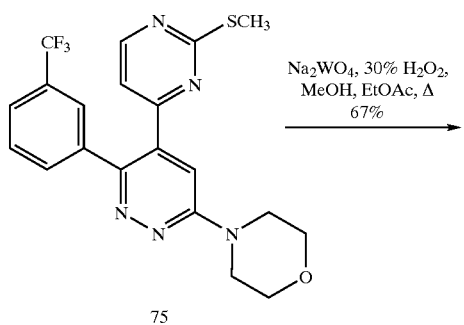
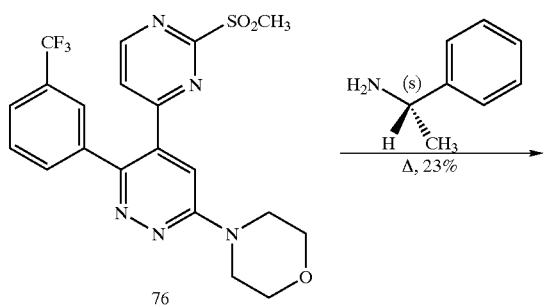
Scheme 4: Synthesis of Compound 78
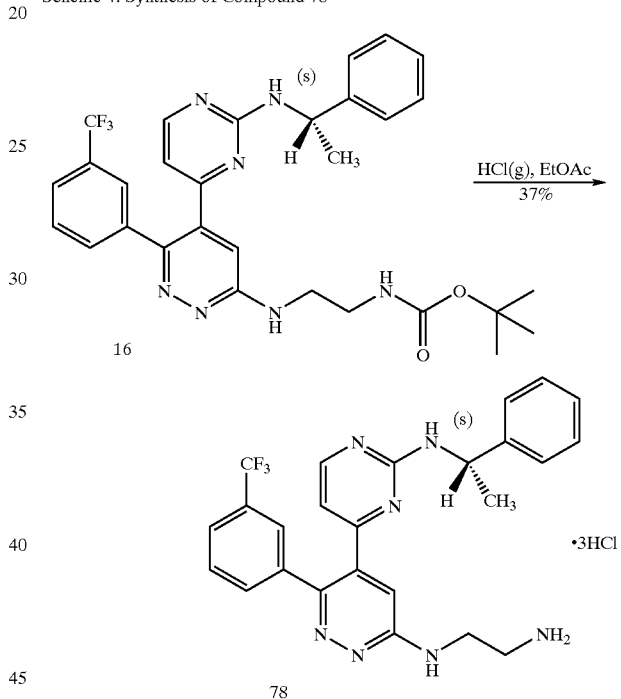
Scheme 5: Synthesis of Compound 82
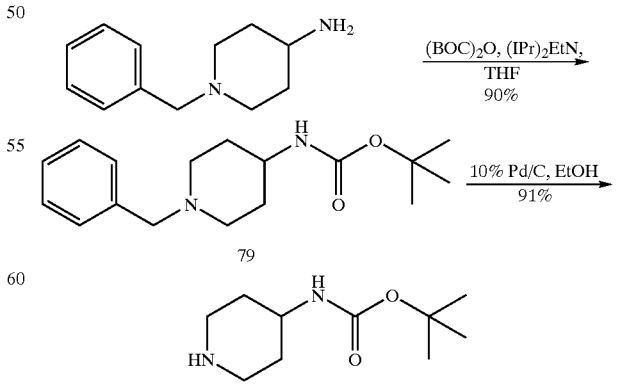

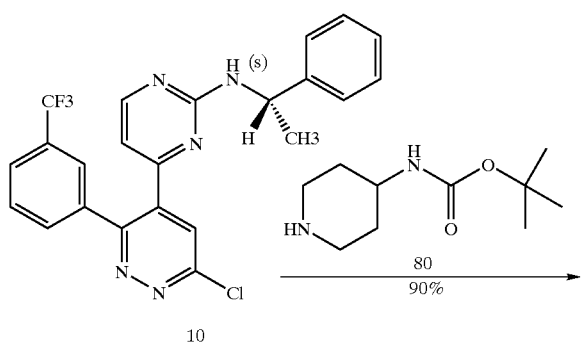
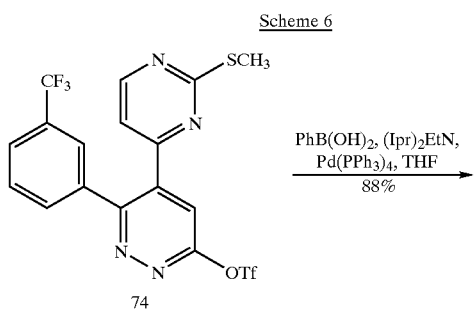
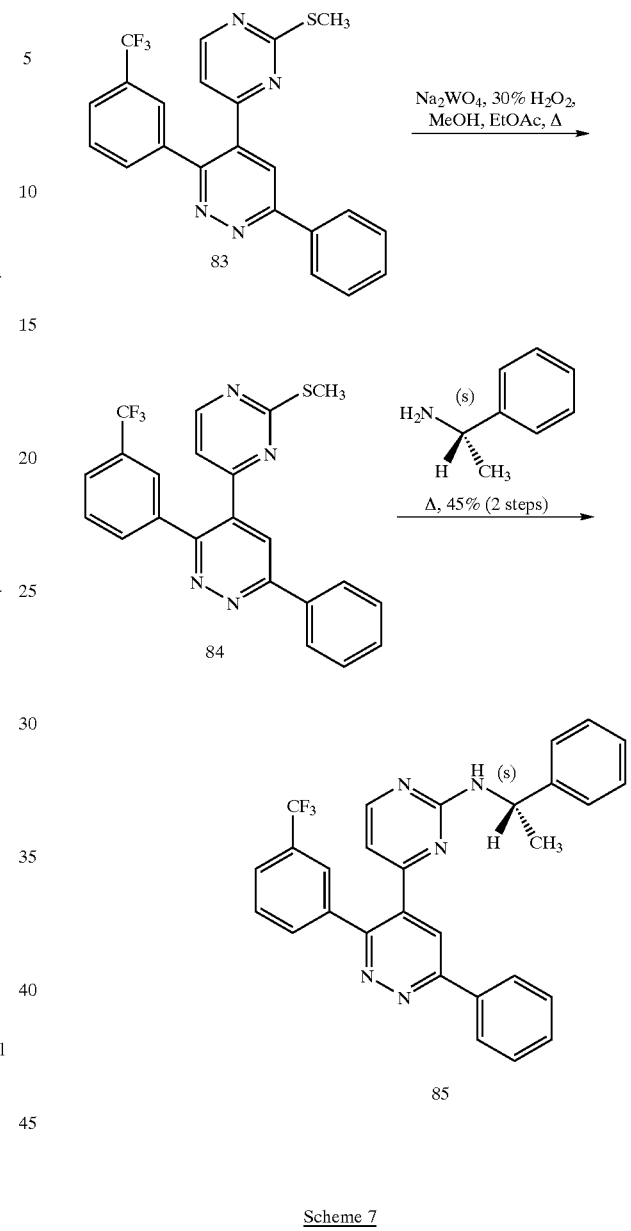
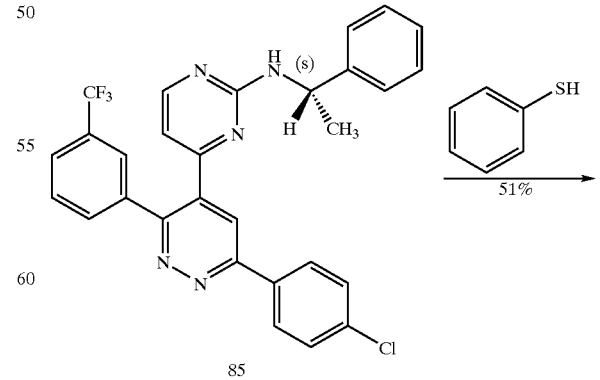

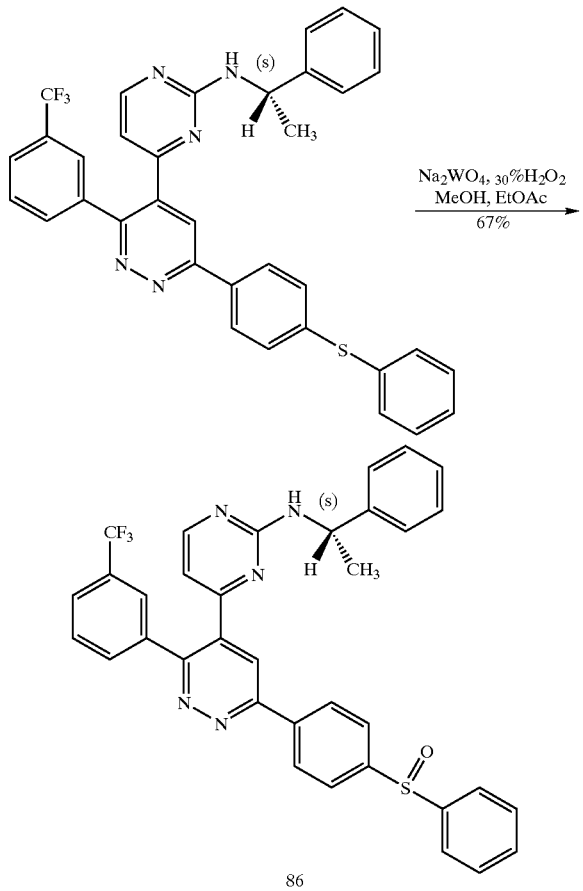

86

The compounds of formula I can be used in the prophylactic or therapeutic treatment of disease states in mammals which are exacerbated or caused by excessive or unregulated cytokines, e.g., IL-1, IL-6, IL-8 or TNF.

Because the compounds of formula I inhibit cytokines, the compounds are useful for treating diseases in which cytokine presence or activity is implicated, such as rheumatoid arthritis, rheumatoid spondylitis, osteoarthritis, gouty arthritis and other arthritic conditions.

The compounds of formula I are useful to treat disease states mediated by excessive or unregulated TNF production or activity. Such diseases include, but are not limited to sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, such as osteoporosis, reperfusion injury, graft v. host rejection, allograft rejection, fever, myalgia due to infection, cachexia secondary to infection or malignancy, cachexia secondary to acquired immune deficiency syndrome (AIDS), AIDS, ARC (AIDs related complex), keloid formation, scar tissue formation, Crohn's disease, ulcerative colitis, pyresis, AIDS and other viral infections, such as cytomegalovirus (CMV), influenza virus, and the herpes family of viruses such as Herpes Zoster or Simplex I and II.

The compounds of formula I are also useful topically in the treatment of inflammation such as in the treatment of rheumatoid arthritis, rheumatoid spondylitis, osteoarthritis, gouty arthritis and other arthritic conditions; inflamed joints, eczema, psoriasis or other inflammatory skin conditions such as sunburn; inflammatory eye conditions including conjunctivitis; pyresis, pain and other conditions associated with inflammation.

The compounds of formula I are also useful in treating diseases characterized by excessive IL-8 activity. These disease states include psoriasis, inflammatory bowel disease, asthma, cardiac and renal reperfusion injury, adult respiratory distress syndrome, thrombosis and glomerulonephritis.

The invention thus includes a method of treating psoriasis, inflammatory bowel disease, asthma, cardiac and renal reperfusion injury, adult respiratory distress syndrome, thrombosis and glomerulonephritis, in a mammal in need of such treatment, which comprises administering to said mammal a compound of formula I in an amount which is effective for treating said disease or condition.

When administered to a patient for the treatment of a disease in which a cytokine or cytokines are implicated, the dosage used can be varied within wide limits, depending upon the type of disease, the age and general condition of the patient, the particular compound administered, the presence or level of toxicity or adverse effects experienced with the drug and other factors. A representative example of a suitable dosage range is from as low as about 0.01 mg/kg to as high as about 100 mg/kg. However, the dosage administered is generally left to the discretion of the physician.

The methods of treatment can be carried out by delivering the compound of formula I parenterally. The term 'parenteral' as used herein includes intravenous, intramuscular, or intraperitoneal administration. The subcutaneous and intramuscular forms of parenteral administration are generally preferred. The instant invention can also be carried out by delivering the compound of formula I through subcutaneous, intranasal, intrarectal, transdermal or intravaginal routes.

The compounds of formula I may also be administered by inhalation. By 'inhalation' is meant intranasal and oral inhalation administration. Appropriate dosage forms for such administration, such as an aerosol formulation or a metered dose inhaler, may be prepared by convention techniques.

The invention also relates to a pharmaceutical composition comprising a compound of formula I and a pharmaceutically acceptable carrier. The compounds of formula I may also be included in pharmaceutical compositions in combination with a second therapeutically active compound.

The pharmaceutical carrier employed may be, for example, either a solid, liquid or gas. Examples of solid carriers include lactose, terra alba, sucrose, talc, gelatin, agar, pectin, acacia, magnesium stearate, stearic acid and the like. Examples of liquid carriers are syrup, peanut oil, olive oil, water and the like. Examples of gaseous carriers include carbon dioxide and nitrogen.

Similarly, the carrier or diluent may include time delay material well known in the art, such as glyceryl monostearate or glyceryl distearate, alone or with a wax.

A wide variety of pharmaceutical dosage forms can be employed. If a solid dosage is used for oral administration, the preparation can be in the form of a tablet, hard gelatin capsule, troche or lozenge. The amount of solid carrier will vary widely, but generally will be from about 0.025 mg to about 1 g. When a liquid dosage form is desired for oral administration, the preparation is typically in the form of a syrup, emulsion, soft gelatin capsule, suspension or solution. When a parenteral dosage form is to be employed, the drug may be in solid or liquid form, and may be formulated for administration directly or may be suitable for reconstitution.

Topical dosage forms are also included. Examples of topical dosage forms are solids, liquids and semi-solids.

Solids would include dusting powders, poultices and the like. Liquids include solutions, suspensions and emulsions. Semi-solids include creams, ointments, gels and the like.

The amount of a compound of formula I used topically will, of course, vary with the compound chosen, the nature and severity of the condition, and can be varied in accordance with the discretion of the physician. A representative, topical, dose of a compound of formula I is from as low as about 0.01 mg to as high as about 2.0 g, administered one to four, preferably one to two times daily.

The active ingredient may comprise, for topical administration, from about 0.001% to about 10% w/w. Drops according to the present invention may comprise sterile or non-sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container aseptically. Examples of bactericidal and fungicidal agents suitable for inclusion in the drops are phenyl-mercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous liquid, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surfactant such as sorbitan esters or polyoxyethylene derivatives thereof. Suspending agents such as natural gums, cellulose derivatives or inorganic materials such as silicas, and other ingredients such as lanolin may also be included.

The following examples illustrate the preparation of some of the compounds of the invention and are not to be construed as limiting the invention disclosed herein.

Example 1

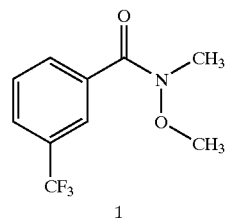

1

N-Methoxy-N-methyl-3-trifluoromethylbenzamide
(1)

3-(Trifluoromethyl)-benzoyl chloride (5 mL, 332 mmol), N,O-dimethyl-hydroxylamine hydrochloride (42 g, 431 mmol) and methylene chloride were combined under argon, then cooled in an ice bath. Triethylamine (108 mL, 775 mmol) was added dropwise with stirring over 0.5 h. The contents of the reaction flask were then warmed to room temperature slowly. After 18 h, the reaction suspension was washed successively with 5% potassium bisulfate, sat. sodium bicarbonate and brine. The organic layer was dried over anhydrous sodium sulfate then concentrated in vacuo to give Compound 1 as an oil: 82 g, (332 mmol, 100%)

$^1$H NMR (CDCl$_3$, 300 MHz) δ 7.98 (s, 1H), 7.88 (d, J=7.8 Hz, 1H), 7.72 (d, J=7.8 Hz, 1H), 7.55 (t, J=7.8 Hz, 1H), 3.55 (s, 3H), 3.39 (s, 3H).

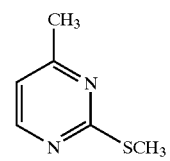

2

4-Methyl-2-methylsulfanylpyrimidine (2)

2-Mercapto-4-methylpyrimidine hydrochloride (100 g, 617 mmol), dimethylformamide dimethylacetal (100 mL, 754 mmol), diisopropylethylamine (161 mL, 926 mmol) and toluene (200 mL) were combined under argon. The resulting solution was heated to reflux for 4 h. The solvent was removed in vacuo and water and sodium bisulfate were added. The resulting mixture was extracted with ether (3×100 mL). The combined organic extracts were washed with brine and dried over anhydrous sodium sulfate. The solvent was removed in vacuo to afford an oil. Vacuum distillation gave Compound 2 as a liquid: 70.5 g, (504 mmol, 82%)

$^1$H NMR (CDCl$_3$, 300 MHz) δ 8.36 (d, J=5.1 Hz, 1H), 6.81 (d, J=5.1 Hz, 1H), 2.56 (s, 3H), 2.46 (s, 3H).

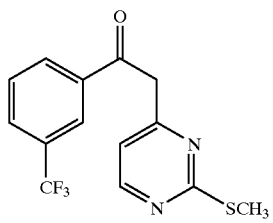

2-(2-Methylsulfanylpyrimidin-4-yl)-1-(3-trifluoromethylphenyl)ethanone (3)

Diisopropylamine (106 mL, 761 mmol) and tetrahydrofuran (THF) 750 mL) were combined in a 3-neck 2L round bottom flask under argon. Two addition funnels, one containing a solution of Compound 1 in THF (100 mL), the other containing Compound 2 in THF (100 mL) were attached to the reaction flask. The contents of the reaction flask were cooled in an IPA/dry ice bath. A solution of n-butyl lithium (2.5M in hexanes, 304 mL, 761 mmol) was added dropwise via syringe. The THF solution of Compound 1 was added dropwise over 0.5 h. This was followed by the addition of the THF solution of Compound 2. A dark solution resulted. After 10 min, ice was added and the THF was removed in vacuo. Water was added followed by sat. sodium bicarbonate and the aqueous mixture was extracted several times with ethyl acetate. The combined organic extracts were washed with brine and dried over anhydrous sodium sulfate. The solvent was removed in vacuo to give an oil. Purification by flash column chromatography (hexane:ethyl acetate 95:5 to 75:25) gave a solid which was triturated with hexane:ether 80:20 then isolated by vacuum filtration to afford Compound 3 as a solid: 60g (220 mmol, 43%)

$^1$H NMR (CDCl$_3$, 300 MHz) δ 14.7 (s, 1H), 8.36 (d, J=5.1 Hz, 1H), 8.09 (s, 1H), 8.01 (d, J=8.1 Hz, 1H), 7.69 (d, J=7.7 Hz, 1H), 7.57 (t, J=7.9 Hz, 1H), 6.70 (d, J=5.5 Hz, 1H), 6.04 (s, 1H), 2.62 (s, 3H).

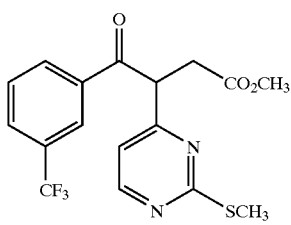

3-(2-Methylsulfanylpyrimidin-4-yl)-4-oxo-4-(3-trifluoromethylphenyl)butyric Acid Methyl Ester (4)

Sodium hydride (95%, 1.78 g, 83 mmol) and dimethyl sulfoxide (DMSO) (150 mL) were combined under argon in a 3-neck 1L round bottom flask. A solution of Compound 3 in DMSO (50 mL) was added dropwise over 0.75 h using an addition funnel. After stirring an additional 0.5 h, methyl bromoacetate (7.9 mL, 83 mmol) in DMSO (50 mL) was added dropwise. After 18 h, the contents of the reaction flask were poured into water. Saturated sodium bicarbonate was added and the resulting solution was extracted several times with ethyl acetate. The combined organic extracts were washed successively with water and brine. The organic layer was dried with anhydrous sodium sulfate then concentrated in vacuo to give an oil. Purification by flash column chromatography (hexane:ethyl acetate 70:30) afforded Compound 4 as an oil: 24.6 g (64 mmol, 100%)

$^1$H NMR (CDCl$_3$, 300 MHz) δ 8.42 (d, J=5.2 Hz, 1H), 8.33 (s, 1H), 8.20 (d, J=7.9 Hz, 1H), 7.80 (d, J=7.9 Hz, 1H), 7.60 (t, J=7.9 Hz, 1H), 6.89 (d, J=5.2 Hz, 1H), 5.30–5.21 (m, 1H), 3.69 (s, 3H), 3.49–3.40 (m, 1H), 2.88 (dd, J=17.2, 4.7 Hz, 1H), 2.49 (s, 3H).

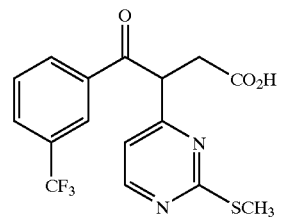

3-(2-Methylsulfanylpyrimidin-4-yl)-4-oxo-4-(3-trifluoromethylphenyl)butyric Acid (5)

A solution of Compound 4 (27.1 g, 64 mmol) and dioxane (500 mL) were stirred under argon. Hydrochloric acid (6N, 250 mL) was added dropwise using an addition funnel. After 3d dioxane was removed in vacuo. The remaining aqueous mixture was extracted exhaustively with methylene chloride. The combined organic extracts were dried over anhydrous sodium sulfate then the solvent was removed in vacuo to give a yellow oil. Hexane followed by ether was added to afford a solid (5) which was isolated by vacuum filtration: 18.6 g (50.4 mmol, 79%)

$^1$H NMR (CDCl$_3$, 300 MHz) δ 8.42 (d, J=5.2 Hz, 1H), 8.33 (s, 1H), 8.20 (d, J=7.9 Hz, 1H), 7.80 (d, J=7.9 Hz, 1H), 7.60 (t, J=7.9 Hz, 1H), 6.89 (d, J=5.2 Hz, 1H), 5.30–5.21 (m, 1H), 3.69 (s, 3H), 3.49–3.40 (m, 1H), 2.88 (dd, J=17.2, 4.7 Hz, 1H), 2.49 (s, 3H).

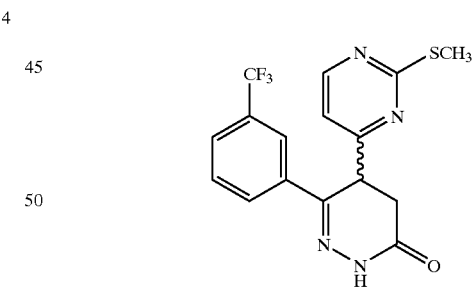

5-(2-Methylsulfanylpyrimidin-4-yl)-6-(3-trifluoromethylphenyl)-4,5-dihydro-2H-pyridazin-3-one (6)

Compound 5 (6.58 g, 17.8 mmol), and ethanol (200 mL) were combined under argon. Hydrazine (835 µL, 26.6 mmol) was added and the resulting solution was heated at reflux for 4 h. The solution was cooled and rotary evaporated. Ethyl acetate was added followed by the addition of ether. The solution was again rotary evaporated to afford a foam (6) which was used as is for the synthesis of 7.

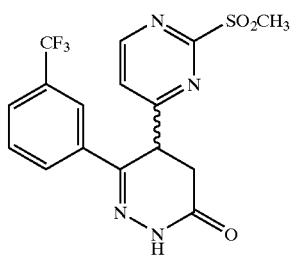

5-(2-Methylsulfonylpyrimidin-4-yl)-6-(3-trifluoromethylphenyl)-4,5-dihydro-2H-pyridazin-3-one (7)

Compound 6 (17.8 mmol), sodium tungstate (587 mg, 1.78 mmol), 30% hydrogen peroxide (8.07 mL, 71.2 mmol), methanol (20 mL), and ethyl acetate (200 mL) were combined under argon, then heated to reflux for 4 h. The solution was cooled and aqueous sodium hydrosulfite was added. The methanol was removed in vacuo and saturated sodium bicarbonate was added. The resulting suspension was extracted several times with methylene chloride. The combined organic extracts were washed successively with water and brine. The organic layer was dried with anhydrous sodium sulfate then concentrated in vacuo to give Compound 7 as a foam: 5.0 g (13 mmol, 73% (two steps))

$^1$H NMR (CDCl$_3$, 300 MHz) δ 8.85 (d, J=5.2 Hz, 1H), 8.79 (s, 1H), 8.11 (s, 1H), 7.88 (d, J=7.9 Hz, 1H), 7.70 (d, J=7.6 Hz, 1H), 7.57 (t, J=7.9 Hz, 1H), 7.33 (d, J=5.2 Hz, 1H), 4.82–4.78 (m, 1H), 3.33 (s, 3H), 3.17–2.05 (m, 2H).

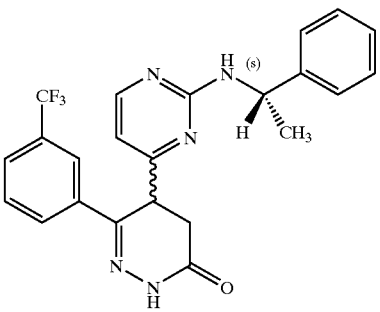

(s)-5-[2-(1-Phenylethylamino)pyrimidin-4-yl]-6-(3-trifluoromethylphenyl)-4,5-dihydro-2H-pyridazin-3-one (8)

Compound 7 (5.00 g, 13.1 mmol), s-(−)-α-methylbenzylamine (3.37 mL, 26.2 mmol) and tetrahydrofuran (100 mL) were heated to reflux under argon for 24 h. The solvent was removed in vacuo. Purification by flash column chromatography (methylene chloride:methanol:ammonium hydroxide 98:2:0.2) gave Compound 8 as a foam: 5.0 g (9.6 mmol, 73%).

$^1$H NMR (CDCl$_3$, 300 MHz) δ 8.62–8.50 (m, 1H), 8.18–8.12 (m, 1H), 8.10–8.00 (m, 1H), 7.80 (d, J=2.7 Hz, 1H), 7.60 (m, 1H), 7.52–7.44 (m, 1H), 7.38–7.20 (m, 5H), 6.33 (t, J=4.3 Hz, 1H), 5.50 (m, 1H), 5.10–5.00 (m, 1H), 4.40–4.30 (m, 1H), 3.10–2.80 (m, 2H), 1.51 (d, J=6.7 Hz, 3H).

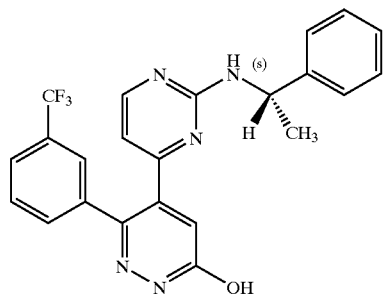

(s)-5-[2-(1-Phenylethylamino)pyrimidin-4-yl]-6-(3-trifluoromethylphenyl)-pyridazin-3-ol (9)

Compound 8 (4.24 g, 9.66 mmol), 2,3-dichloro-5,6-dicyano-4-benzoquinone (4.38 g, 19.3 mmol), and acetonitrile (100 mL) were combined and stirred at room temperature under argon for 24 h. The solvent was removed in vacuo and 5% ammonium hydroxide was added. The solution was extracted exhaustively with methylene chloride. The combined organic extracts were dried over anhydrous sodium sulfate and the solvent was removed in vacuo to give a solid. Trituration with hexane-ether gave Compound 9 as a solid: 3.5 g (8.0 mmol, 82%)

$^1$H NMR (CDCl$_3$, 300 MHz) δ 12.20–12.00 (s, br, 1H), 8.24 (d, J=4.9 Hz, 1H), 7.64–7.56 (m, 2H), 7.42–7.20 (m, 8H), 6.40–6.34 (m, 1H), 5.80 (s, br, 1H), 4.80 (s, br, 1H), 1.25 (m, br, 3H).

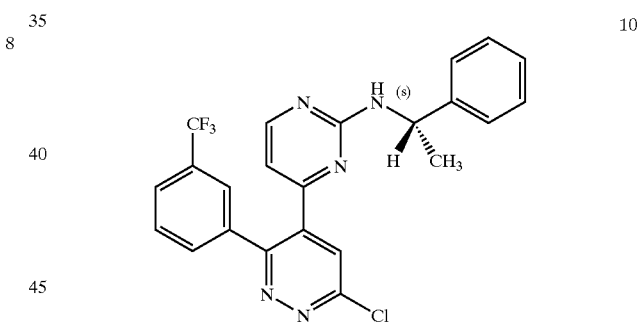

(s)-6-Chloro-4-[2-(1-phenylethylamino)pyrimidin-4-yl]-3-(3-trifluoromethyl-phenyl)pyridazine (10)

Compound 9 (3.5 g, 7.96 mmol) and phosphorus oxychloride (20 mL) were combined under argon then heated at 90° C. for 0.5 h. The solution was cooled and poured onto ice. The resulting suspension was made basic with 2N sodium hydroxide and extracted several times with methylene chloride. The combined organic extracts were washed with brine and dried with anhydrous sodium sulfate. Evaporation of the solvent in vacuo gave an oil which was purified by flash column chromatography (hexane ethyl acetate 80:20) to give Compound 10 as a foam: 2.9 g (6.4 mmol, 80%)

$^1$H NMR (CDCl$_3$, 300 MHz) δ 8.16 (d, J=4.9 Hz, 1H), 7.83 (s, 1H), 7.72–7.45 (m, 4H), 7.40–7.25 (m, 5H), 6.21 (d, J=4.9 Hz, 1H), 5.65–5.55 (s, br, 1H), 5.05–4.90 (s, br, 1H), 1.51 (d, J=7.0 Hz, 3H).

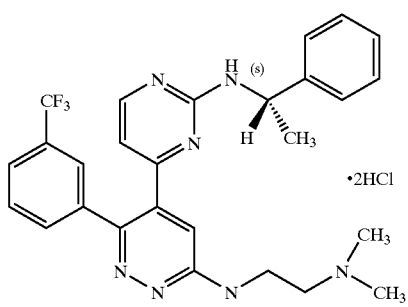

(s)-N-1-{5-[2-(1-Phenethyl)aminopyrimidin-4-yl]-6-(3-trifluoromethylphenyl)-pyridazin-3-yl}-N-2-(dimethyl)ethane-1,2-diamine Dihydrochloride (11)

Compound 10 (100 mg, 0.220 mmol), and dimethylethylenediamine (~500 μL) were combined under argon and heated at 100° C. for 1 h. The contents of the reaction flask were poured into saturated sodium bicarbonate and extracted several times with methylene chloride. The combined organic portions were dried with anhydrous sodium sulfate and concentrated in vacuo. Purification by flash column chromatography (methylene chloride:methanol:ammonia 95:5:0.5) gave a foam which was dissolved in ether. Addition of 1N hydrogen chloride in ether gave Compound 11 as a solid: 8 mg (0.152 mmol, 69%)

$^1$H NMR (CD$_3$OD, 300 MHz) δ 8.42–8.32 (m, 1H), 7.84–7.68 (m, 3H), 7.66–7.58 (m, 2H), 7.32–7.16 (m, 5H), 6.96–6.80 (s, br, 1H), 3.99 (t, J=6.0 Hz, 2H), 3.54 (t,=6.0 Hz, 2H), 3.01 (s, 6H), 1.45–1.25 (s, br, 3H).

Compounds 12–68 were prepared in a manner similar to that described for the preparation of 11. Mass spectrometry was used to characterize either free base, hydrochloride salt, or trifluoroacetic acid salt of compounds 12–68. These compounds are summarized below in Table 1.

TABLE 1

Reaction of 10 With 1° or 2° Amines

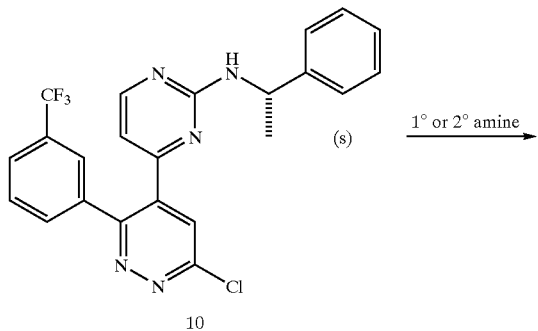

TABLE 1-continued

| Number | R | MS [M + H]$^+$ | Salt Form |
|---|---|---|---|
| 12 | ～N(H)～～OCH$_3$ | 509.3 | free base |
| 13 | ～N(H)～～OCH$_2$OCH$_3$ | 523.2 | free base |
| 14 | ～N(H)～～(imidazol-1-yl) | 546.3 | free base |
| 15 | ～N(H)–(1-benzylpiperidin-4-yl) | 610.2 | free base |
| 16 | ～N(H)CH$_2$CH$_2$NHC(O)OC(CH$_3$)$_3$ | 581.2 | .2 HCl |
| 17 | ～N(H)CH$_2$–(3,4-dimethoxyphenyl) | 587.0 | .2 HCl |
| 18 | ～(1,4-dioxa-8-azaspiro[4.5]dec-8-yl) | 563.0 | free base |
| 19 | ～(imidazol-1-yl) | 488.3 | free base |

TABLE 1-continued
| | | | | |
|---|---|---|---|---|
| 20 | 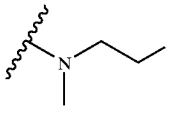 | 520.2 | .3 HCl | |
| 21 | 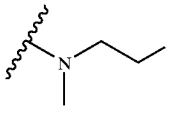 | 506.1 | .3 HCl | |
| 22 | 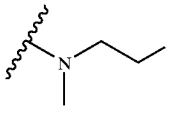 | 553.5 | .2 TFA | |
| 23 | 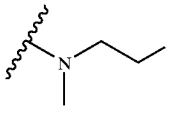 | 533.3 | .2 TFA | |
| 24 | 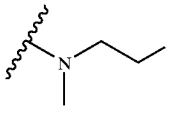 | 588.0 | .3 TFA | |
| 25 | 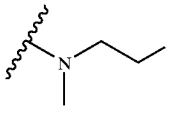 | 535.4 | .3 TFA | |
| 26 | 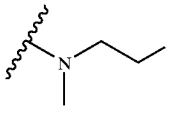 | 534.1 | .3 TFA | |
| 27 | 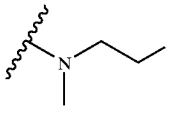 | 600.2 | .3 TFA | |
| 28 | 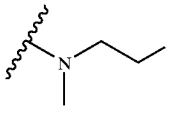 | 519.1 | .2 TFA | |
| 29 | 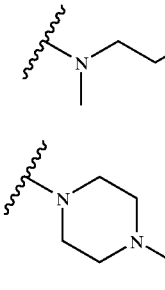 | 519.2 | .2 TFA | |
| 30 | 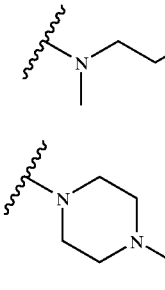 | 522.2 | .3 TFA | |
| 31 | 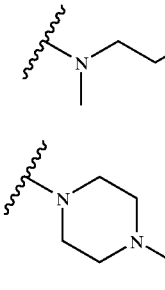 | 582.5 | .3 TFA | |
| 32 | 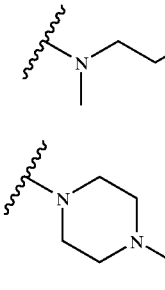 | 559.4 | .2 TFA | |
| 33 | 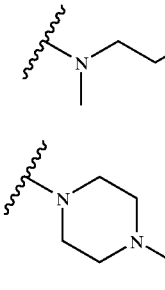 | 505.5 | .1 HCl | |
| 34 | 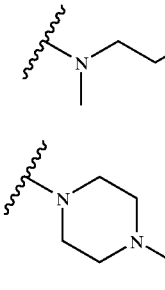 | 553.5 | .2 TFA | |
| 35 | 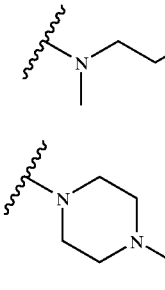 | 533.3 | .2 TFA | |
| 36 | 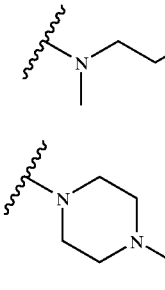 | 708.6 | .3 TFA | |
| 37 | 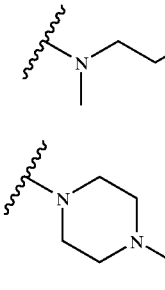 | 535.2 | .2 TFA | |

TABLE 1-continued

| # | Structure | MS | Salt |
|---|---|---|---|
| 38 | thiomorpholine | 523.2 | .2 TFA |
| 39 | 4-phenylpiperidine | 581.2 | .2 TFA |
| 40 | N-ethyl-N-benzylamine | 555.2 | .2 TFA |
| 41 | di-n-butylamine | 549.3 | .2 TFA |
| 42 | 4-(3,4-dimethylphenyl)piperazine | 610.2 | .3 TFA |
| 43 | 3-methyl-4-phenylpiperazine | 596.4 | .3 TFA |
| 44 | 3-methyl-4-(4-methoxyphenyl)piperazine | 626.2 | .2 TFA |
| 45 | homopiperidine | 519.3 | .2 TFA |
| 46 | N-methyl-N-propargylamine | 489.2 | .2 TFA |
| 47 | 3-(ethoxycarbonyl)piperidine | 577.4 | .2 TFA |
| 48 | 4-(dimethylamino)-1-methylpiperidine | 548.3 | .3 TFA |
| 49 | 2-methylpiperidine | 519.5 | .2 TFA |
| 50 | N,N-bis(2-phenylethyl)amine | 631.0 | .2 TFA |
| 51 | N-methyl-N-(2-(2-pyridyl)ethyl)amine | 556.2 | .2 TFA |
| 52 | 3-(N,N-diethylcarbamoyl)piperidine | 604.4 | .2 TFA |
| 53 | 3-carbamoylpiperidine | 548.4 | .2 TFA |
| 54 | 4-carbamoylpiperidine | 548.2 | .2 TFA |
| 55 | N-methyl-N-(2-(indol-3-yl)ethyl)amine | 594.2 | .2 TFA |
| 56 | 4-hydroxy-4-phenylpiperidine | 597.4 | .2 TFA |

TABLE 1-continued

| | | | |
|---|---|---|---|
| 57 | (4-chlorophenyl-4-hydroxypiperidine) | 631.2 | .2 TFA |
| 58 | (4-bromophenyl-4-hydroxypiperidine) | 677.4 | .2 TFA |
| 59 | (N-propyl-N-(2-methoxyethyl)amine) | 537.9 | .2 TFA |
| 60 | (N-ethyl-N-(2-methoxyethyl)amine) | 523.3 | .2 TFA |
| 61 | (N-methyl-N-(2-methoxyethyl)amine) | 509.0 | .2 TFA |
| 62 | (2-methylimidazol-1-yl) | 502.0 | .1 TFA |
| 63 | (4-methyl-2-phenylimidazol-1-yl) | 578.8 | .1 TFA |
| 64 | (2-phenylimidazol-1-yl) | 563.9 | .1 TFA |
| 65 | (4-(1,3-benzodioxol-5-ylmethyl)piperazin-1-yl) | 640.2 | .3 TFA |

TABLE 1-continued

| | | | |
|---|---|---|---|
| 66 | (4-(ethoxycarbonyl)piperazin-1-yl) | 578.5 | .2 TFA |
| 67 | (N-ethyl-N-(2-(dimethylamino)ethyl)amine) | 535.9 | .3 TFA |
| 68 | (4-(2,5-dimethylphenyl)piperazin-1-yl) | 611.0 | .3 TFA |

EXAMPLE 2

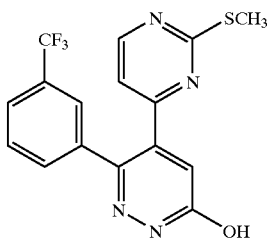

5-(2-Methylsulfanylpyrimidin-4-yl)-6-(3-trifluoromethylphenyl)pyridazin-3-ol (69)

Compound 6 (1.92 g, 5.26 mmol), 2,3-dichloro-5,6-dicyano-1,4-benzoquinone (4.78 g, 21.0 mmol), and acetonitrile (30 mL) were combined under argon and heated at 90° C. for 1 h. The solution was cooled and the solvent was removed in vacuo. The crude product was purified by flash column chromatography (methylene chloride:methanol:ammonium hydroxide 95:5:0.5) to give a solid. Trituration with.$Et_2O$ EtOAc gave Compound 69: 1.60 g (4.4 mmol, 83%)

$^1$H NMR ($CDCl_3$, 300 MHz) δ 12.95 (s, 1H), 8.51 (d, J=4.9 Hz, 1H), 7.67–7.61 (m, 2H), 7.46–7.39 (m, 1H), 7.34–7.27 (m, 2H), 6.84 (d, J=5.2 Hz, 1H), 2.25 (s, 3H).

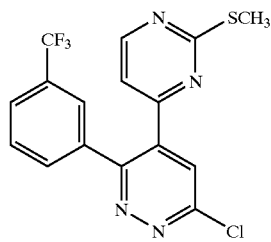

6-Chloro-4-(2-methylsulfanylethylpyrimidin-4-yl)-3-(3-trifluoromethylphenyl)-pyridazine (70)

Compound 69 (1.32 g, 3.63 mmol) and phosphorus oxychloride (10 mL) were combined under argon and heated at 90° C. for 1 h. The solution was cooled and excess phosphorus oxychloride was removed in vacuo. Water was added followed by sat. sodium bicarbonate and the solution was extracted several times with ethyl acetate. The combined organic extracts were washed with brine and dried with anhydrous sodium sulfate. Evaporation of the solvent in vacuo gave a solid. Purification by flash column chromatography (hexane ethyl acetate 70:30) gave an oil which was crystallized using hexane:ethyl acetate 90:10 to give Compound 70: 937 mg (2.45 mmol, 67%)

$^1$H NMR (CDCl$_3$, 300 MHz) δ 8.45 (d, J=4.9 Hz, 1H), 7.91 (s, 1H), 7.86 (s, 1H), 7.76–7.70 (m, 1H), 7.58–7.48 (m, 2H), 6.69 (d, J=5.2 Hz, 1H), 2.45 (s, 3H).

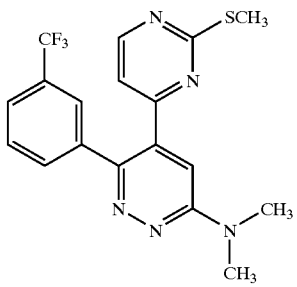

Dimethyl-[5-(2-methylsulfanylpyrimidin-4-yl)-6-(3-trifluoromethylphenyl)-pyridazin-3-yl]amine (71)

Compound 70 (200 mg, 0.522 mmol) and ethanol (4 mL) were combined in a threaded glass pressure tube. The reaction solution was cooled in an ice bath and dimethylamine was bubbled through the solution until saturated. The solution was sealed and heated to 60° C. for 24 h. The solvent was removed in vacuo. Purification by flash column chromatography (hexane:ethyl acetate 60:40) gave an oil which crystallized from hexane: ethyl acetate to afford Compound 71: 128 mg (0.327 mmol, 63%)

$^1$H NMR (CDCl$_3$, 300 MHz) δ 8.39 (d, J=5.2 Hz, 1H), 7.85 (s, 1H), 7.58 (d, J=7.3 Hz, 1H), 7.48–7.36 (m, 2H), 7.07 (s, 1H), 6.67 (d, J=5.2 Hz, 1H), 3.30 (s, 6H), 2.45 (s, 3H).

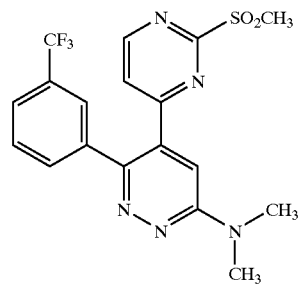

Dimethyl-[5-(2-methylsulfonylpyrimidin-4-yl)-6-(3-trifluoromethylphenyl)-pyridazin-3-yl]amine (72)

Compound 71 (112 mg, 0.286 mmol), sodium tungstate (10 mg, 0.02 mmol), 30% hydrogen peroxide (130 μL, 1.14 mmol), methanol (2.0 mL), and ethyl acetate (20 mL) were combined under Argon and heated to reflux for 3d. The solution was cooled, poured into water and extracted several times with ethyl acetate. The combined organic extracts were dried with anhydrous sodium sulfate. Removal of the solvent in vacuo gave 72 as a solid: 109 mg (0.259 mmol, 91%)

$^1$H NMR (CDCl$_3$, 300 MHz) δ 8.77 (d, J=5.2 Hz, 1H), 7.82 (s, 1H), 7.66–7.60 (m, 1H), 7.48–7.42 (m, 2H), 7.24–7.20 (m, 1H), 7.15 (s, 1H), 3.33 (s, 6H), 3.27 (s, 3H).

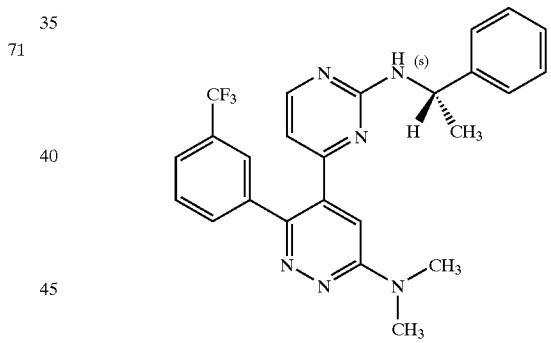

(s)-Dimethyl-{5-[2-(1-phenethyl)aminopyrimidin-4-yl]-6-(3-trifluoromethyl-phenyl)pyridazin-3-yl}amine (73)

Compound 72 (155 mg, 0.367 mmol) and s-(−)-α-methylbenzylamine (0.500 mL) were combined under Argon and heated at 100° C. for 0.5 h. The solution was cooled and purified by flash column chromatography (hexane:ethyl acetate 50:50) to give an oil which was crystallized using hexane ethyl acetate ether to give Compound 73: 80mg (0.172 mmol, 47%)

$^1$H NMR (CDCl$_3$, 300 MHz) δ 8.12 (d, J=5.2 Hz, 1H), 7.83 (s, 1H), 7.54 (t, J=9.0 Hz, 2H), 7.40–7.20 (m, 6H), 6.85 (s, 1H), 6.21 (d, J=4.9 Hz, 1H), 5.51 (d, J=7.3 Hz, 1H), 5.10–5.00 (s, br, 1H), 3.22 (s, 6H), 1.51 (d, J=6.7 Hz, 3H).

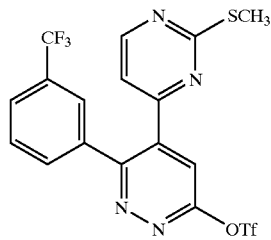

Trifluoromethanesulfonic Acid 5-(2-methylsulfanylpyrimidine-4-yl)-6-(3-trifluoromethylphenyl)pyridazin-3-yl Ester (74)

Compound 69 (2.59 g, 7.11 mmol), and methylene chloride (100 mL) were combined under argon and cooled in an ice bath. Diisopropylethylamine (1.61 mL, 9.24 mmol) was added followed by trifluoromethanesulfonic anhydride (1.58 mL, 9.24 mmol). After 1 h, the solvent was removed in vacuo. Flash column chromatography (hexane: ethyl acetate 80:20) followed by trituration with hexane and ether afforded Compound 74 as a solid: 3.15 g (6.37 mmol, 89%)

$^1$H NMR (CDCl$_3$, 300 MHz) δ 8.48 (d, J=4.9 Hz, 1H), 7.90 (s, 1H), 7.84 (s, 1H), 7.80–7.74 (m, 1H), 7.62–7.50 (m, 2H), 6.70 (d, J=5.2 Hz, 1H), 2.47 (s, 3H).

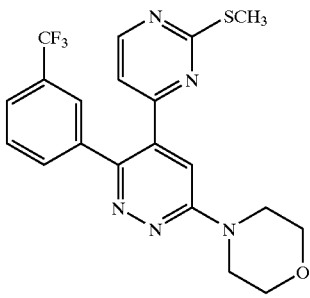

4-[5-(2-Methylsulfanylpyrimidin-4-yl)-6-(3-trifluoromethylphenyl)-pyridazin-3-yl]morpholine (75)

Compound 74 (180 mg, 0.363 mmol) and morpholine (~1 mL) were combined under Argon and heated to 80° C. for 2 h. Purification by flash column chromatography (hexane ethyl acetate 50:50) gave Compound 75 as an oil: 104 mg (0.240 mmol, 66%)

$^1$H NMR (CDCl$_3$, 300 MHz) δ 8.39 (d, J=5.2 Hz, 1H), 7.86 (s, 1H), 7.64–7.59 (m, 1H), 7.50–7.38 (m, 2H), 7.20 (s, 1H), 6.65 (d, J=4.9 Hz, 1H), 3.95–3.85 (m, 4H), 3.85–3.75 (m, 4H), 2.46 (s, 3H).

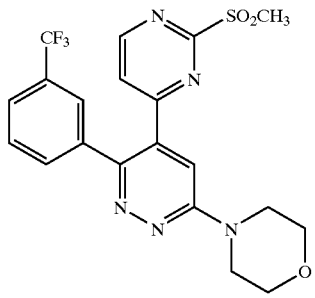

4-[5-(2-Methylsulfonylpyrimidin-4-yl)-6-(3-trifluoromethylphenyl)-pyridazin-3-yl]morpholine (76)

Compound 75 (104 mg, 0.240 mmol), sodium tungstate (7 mg, 0.02 mmol), 30% hydrogen peroxide (109 μL, 0.960 mmol), methanol (500 μL), and ethyl acetate (5 mL) were combined under Argon and heated to reflux for 3d. The solvent was removed in vacuo followed by flash column chromatography (ethyl acetate hexane 90:10) to afford Compound 76 as a solid: 75 mg (0.161 mmol, 67%)

$^1$H NMR (CDCl$_3$, 300 MHz) δ 8.75 (d, J=5.2 Hz, 1H), 7.82 (s, 1H), 7.70–7.62 (m, 1H); 7.50–7.42 (m, 2H), 7.32–7.24 (m, 1H), 7.17 (d, J=5.2 Hz, 1H), 3.95–3.85 (m, 4H), 3.85–3.75 (m, 4H), 3.31 (s, 3H).

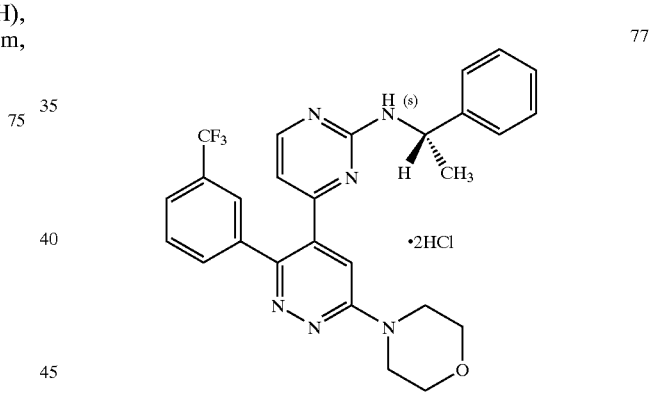

(s)-4-{5-[2-(1-Phenethylamino)pyrimidin-4-yl]-6-(3-trifluoromethylphenyl)-pyridazin-3-yl}morpholine dihydrochloride (77)

Compound 76 (75 mg, 0.161 mmol) and s-(−)-α-methylbenzylamine (500 μL) were combined under Argon and heated at 100° C. for 0.5 h. Flash column chromatography (hexane:ethyl acetate 70:30) of the reaction mixture gave a mixture of the desired product and s-(−)-α-methylbenzylamine. Ethyl acetate was added and the mixture was washed with 5% potassium bisulfate. The organic layer was dried with anhydrous sodium sulfate and the solvent was removed in vacuo to give a foam. Treatment with 1N hydrogen chloride/ether gave Compound 77 as a solid: 33 mg (0.057 mmol, 35%)

$^1$H NMR (CD$_3$OD, 300 MHz) δ 8.46–8.34 (s, br, 1H), 8.14–8.04 (s, br, 1H), 7.84–7.74 (m, 2H), 7.66–7.58 (m, 2H), 7.32–7.14 (m, 5H), 7.02–6.88 (s, br, 1H), 4.60–4.40 (s, br, 1H), 3.95–3.80 (m, 8H), 1.45–1.30 (s, br, 3H).

EXAMPLE 4

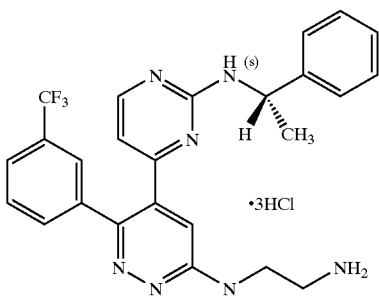

(s)-N-1-{5-[2-(1-Phenethyl)aminopyrimidin-4-yl]-6-(3-trifluoromethylphenyl)-pyridazin-3-yl}ethane-1,2-diamine Trihydrochloride (78)

Compound 16 (210 mg, 0.363 mmol) and ethyl acetate (15 mL) were combined under Argon and cooled in an ice bath. The solution was saturated with hydrogen chloride gas. The mixture was stirred with cooling for 0.5 h and warmed to room temperature for 1 h. Removal of the solvent in vacuo gave a solid which as triturated with acetonitrile to afford 80 mg (0.136 mmol, 37%) of Compound 31:

$^1$H NMR (CD$_3$OD, 300 MHz) δ 8.38–8.30 (m, 1H), 8.22–8.16 (m, 1H), 7.94–7.86 (m, 2H), 7.80–7.70 (m, 2H), 7.66–7.50 (m, 5H), 7.32–7.18 (m, 5H), 6.52–6.44 (s, br, 1H), 1.44–1.36 (m, 3H).

EXAMPLE 5

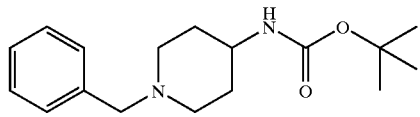

1-Benzyl-4-(tert-butoxycarbonylamino)piperidine (79)

4-Amino-1-benzylpiperidine (5.0 mL, 24.6 mmol) tetrahydrofuran (70 mL), and diisopropylethylamine (10.3 mL, 59.1 mmol) were combined under Ar and cooled in an ice bath. Di-tert-butyl dicarbonate (6.45 g, 29.6 mmol) in tetrahydrofuran (30 mL) was added dropwise. The reaction solution was allowed to warm to room temperature and stirred 24 h. The solvent was removed in vacuo and the remaining residue was purified by flash column chromatography (hexane:ethyl acetate 70:30) to give a solid. Trituration with ether gave 6.44 g (22.2 mmol, 90.3%) of Compound 79 as a solid.

$^1$H NMR (CDCl$_3$, 300 MHz) δ 7.30–7.26 (m, 5H), 4.45–4.35 (s, br, 1H), 3.48 (s, 3H), 2.85–2.75 (m, 2H), 2.15–2.05 (m, 2H), 1.95–1.85 (m, 2H), 1.44 (s, 11H).

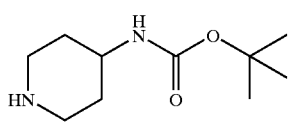

4-(tert-Butoxycarbonylamino)piperidine (80)

Compound 79 (4.55 g, 15.7 mmol), 10% palladium on carbon (400 mg), and ethanol (100 mL) were combined and hydrogenated in a Parr jar at 63psi for 3d. The mixture was filtrated through celite, followed by removal of the solvent in vacuo to afford 2.87 g (14.4 mmol, 91.4%) of Compound 80.

$^1$H NMR (CDCl$_3$, 300 MHz) δ 4.52–4.40 (s, br, 1H), 3.60–3.45 (s, br, 1H), 3.10–3.00 (m, 2H), 2.72–2.57 (m, 2H), 2.00–1.88 (m, 2H), 1.45 (s, 9H), 1.35–1.18 (m, 2H).

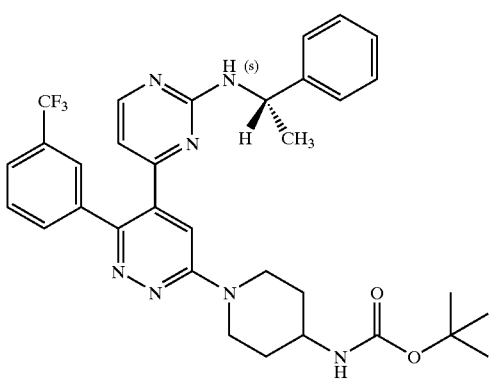

(s)-1-{5-[2-(1-Phenethylamino)pyrimidin-4-yl]-6-(3-trifluoromethylphenyl)-pyridazin-3-yl}-4-(tert-Butoxycarbonylamino)piperidine (81)

Compound 10 (320 mg, 0.701 mmol), Compound 80 (421 mg, 2.10 mmol), and toluene (2 mL) were combined under Argon and heated to 110° C. for 8 h. The contents of the reaction flask were poured into 5% potassium bisulfate and extracted several times with methylene chloride. The combined organic extracts were washed with brine and dried with anhydrous sodium sulfate. Purification by flash column chromatography (hexane:ethyl acetate 50:50) afforded 391 mg (0.632 mmol, 90%) of Compound 81 as a foam.

$^1$H NMR (CDCl$_3$, 300 MHz) δ 8.11 (d, J=5.2 Hz, 1H), 7.83 (s, 1H), 7.60–7.50 (m,2H), 7.42–7.22 (m, 6H), 6.96–6.88 (s, br, 1H), 6.17 (d, J=4.9 Hz, 1H), 5.53 (d, J=7.6 Hz, 1H), 5.10–5.00 (s, br, 1H), 4.54–4.30 (m, 3H), 3.86–3.70 (m, 1H), 3.20–3.08 (m, 2H), 2.14–2.04 (m, 2H), 1.60–1.44 (m, 12H), 1.30–1.24 (m, 2H).

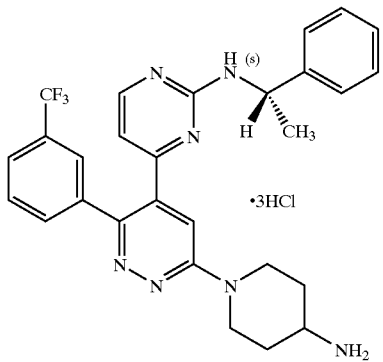

(s)-1-{5-[2-(1-Phenethylamino)pyrimidin-4-yl]-6-(3-trifluoromethylphenyl)-pyridazin-3-yl}-4-aminopiperidine Trihydrochloride (82)

Compound 81 (391 mg, 0.632 mmol) and ethyl acetate (20 mL) were combined under Ar and cooled in an ice bath.

The solution was saturated with hydrogen chloride gas. An oil appeared in the reaction flask. Addition of ethanol (5 mL) gave a solution. The solution was stirred for 1 h and the solvent was removed in vacuo. The remaining residue was triturated with ethyl acetate to afford 313 mg (0.498 mmol, 79%) of Compound 82 as a solid.

$^1$H NMR (CD$_3$OD, 300 MHz) δ 8.56–8.48 (s, br, 1H), 8.37 (s, 1H), 7.88–7.79 (m, 2H), 7.70–7.64 (m, 2H), 7.36–7.16 (m, 6H), 4.65–4.55 (m, 3H), 3.70–3.45 (m, 3H), 2.35–2.25 (m, 2H), 2.05–1.85 (m, 2H), 1.45–1.35 (m, 3H).

EXAMPLE 6

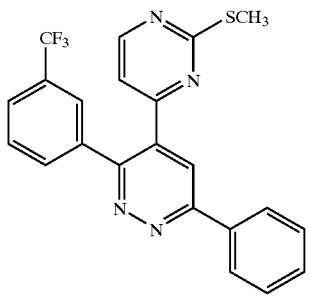

83

4-(2-Methylsulfanylpyrimidin-4-yl)-6-phenyl-3-(3-trifluoromethylphenyl)-pyridazine Compound 74 (112 mg, 0.23 mmol), phenylboronic acid (33 mg, 0.27 mmol), diisopropylethylamine (141 μL, 0.81 mmol), tetrakis(triphenylphosphine)-palladium(0) (26 mg, 0.023 mmol), and tetrahydrofuran (2 mL) were combined under argon and heated at reflux for 24 h. The mixture was cooled and poured into water and sat. sodium bicarbonate. The resultant solution was extracted several times with ether. The combined organic extracts were dried with anhydrous sodium sulfate and the solvent was removed in vacuo. Purification by flash column chromatography (hexane:ethyl acetate 80:20 then 60:40) gave 84 mg (0.20 mmol, 88%) of Compound 83 as an oil:

$^1$H NMR (CDCl$_3$, 300 MHz) δ 8.45 (d, J=4.9 Hz, 1H), 8.28–8.16 (m, 3H), 7.97 (s, 1H), 7.74–7.68 (m, 1H), 7.64–7.48 (m, 5H), 6.79 (d, J=5.2 Hz, 1H), 2.45 (s, 3H).

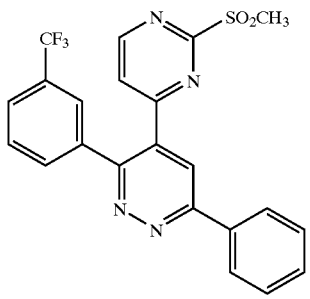

84

4-(2-Methylsulfonylpyrimidin-4-yl)-6-phenyl-3-(3-trifluoromethylphenyl)-pyridazine Compound 83 (80 mg, 0.189 mmol), sodium tungstate (7 mg, 0.02 mmol), 30% hydrogen peroxide (86 μL, 0.77 mmol), methanol (1 mL) and ethyl acetate (5 mL) were combined under argon and heated at a gentle reflux for 24 h. The mixture was cooled and the solvent was removed in vacuo to afford Compound 84.

$^1$H NMR (CDCl$_3$, 300 MHz) δ 8.85 (d, J=5.2 Hz, 1H), 8.30 (s, 1H), 8.26–8.18 (m, 2H), 7.96 (s, 1H), 7.78–7.73 (m, 1H), 7.64–7.50 (m, 5H), 7.33 (d, J=5.2 Hz, 1H), 3.30 (s, 3H).

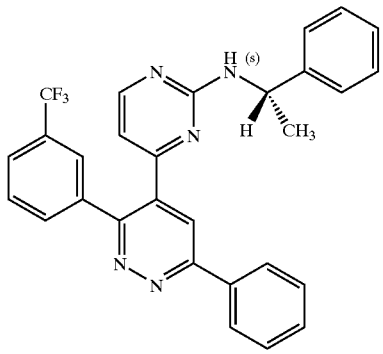

85

(s)-6-Phenyl-4-[2-(1-phenylethylamino)pyrimidin-4-yl]-3-(3-trifluoromethylphenyl)pyridazine (85)

Compound 84 (0.189 mmol) and s-(−)-α-methylbenzylamine (0.500 mL) were combined under Ar and heated at 100° C. for 1 h. The mixture was cooled and purified by flash column chromatography (hexane:ethyl acetate 70:30) to give an oil which was crystallized using hexane:ethyl acetate ether to give 42 mg (0.085 mmol, 45%) of Compound 85.

$^1$H NMR (CDCl$_3$, 300 MHz) δ 8.22–8.10 (m, 3H), 7.95 (s, br, 2H), 7.67 (d, J=7.9 Hz, 2H), 7.61–7.45 (m, 4H), 7.40–7.25 (m, 5H), 6.29 (d, J=4.9 Hz, 1H), 5.57 (d, J=7.3 Hz, 1H), 5.10–5.00 (s, br, 1H), 1.58–1.50 (m, 3H).

EXAMPLE 7

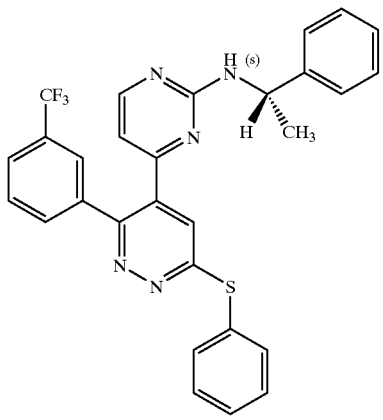

86

(s)-5-[2-(1-Phenylethylamino)pyrimidin-4-yl]-3-(phenylsulfanyl)-6-(3-trifluoromethylphenyl)pyridazine (86)

Compound 10 (100 mg, 0.220 mmol), thiophenol (~200 μL), and diisopropylethylamine (100 mL) were combined under Ar and heated at 120° C. for 3 h. The mixture was purified by flash column chromatography (hexane:ethyl acetate 70:30) to afford a foam. Crystallization from hexane:ethyl acetate afforded 59 mg (0.112 mmol, 51%) of Compound 86.

$^1$H NMR (DMSO-d$_6$, 300 MHz) δ 8.30–8.20 (s, br, 1H), 7.90–7.68 (m, 4H), 7.68–7.52 (m, 5H), 7.48 (s, 1H), 7.30–7.10 (m, 5H), 6.56–6.44 (s, br, 1H), 5.20–4.80 (s, br, 1H), 4.40 (s, br, 1H), 1.40–1.00 (m, 3H).

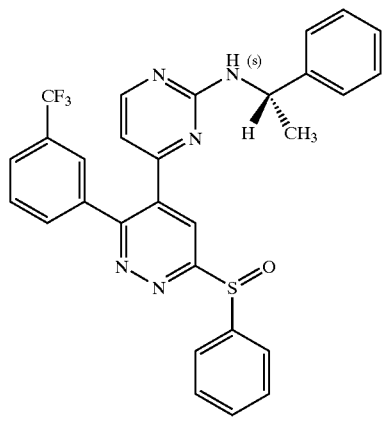

(s)-5-[2-(1-Phenylethylamino)pyrimidin-4-yl]-3-(phenylsulfinyl)-6-(3-trifluoromethylphenyl)pyridazine (87)

Compound 86 (70 mg, 0.132 mmol), sodium periodate (28 mg, 0.132 mmol), methanol (2 mL) and water (250 µL) were combined at 0° C. under Argon. After 0.5 h, the mixture was warmed to room temperature and stirred for 24 h. An additional portion of sodium periodate (28 mg, 0.132 mmol) was added and heated to 60° C. for 48 h. Ethyl acetate and water were added. The layers were separated and the organic portion was dried with anhydrous sodium sulfate. The solvent was removed in vacuo and the remaining residue was purified by flash column chromatography (hexane:ethyl acetate 50:50) to give 20 mg (0.036 mmol, 28%) of Compound 87 as a foam.

$^1$H NMR (CD$_3$OD, 300 MHz) δ 8.38–8.30 (m, 1H), 8.22–8.16 (m, 1H), 7.94–7.86 (m, 2H), 7.80–7.70 (m, 2H), 7.66–7.50 (m, 5H), 7.32–7.18 (m, 5H), 6.52–6.44 (m, br, 1H), 1.44–1.36 (m, 3H).

The ability of compounds of the present invention to inhibit the synthesis or the activity of cytokines can be demonstrated using the following in vitro assays.

BIOLOGICAL ASSAYS

Lipopolysaccharide Mediated Production of Cytokines

Human peripheral blood mononuclear cells (PBMC) are isolated from fresh human blood according to the procedure of Chin and Kostura, *J. Immunol.* 151, 5574–5585 (1993). Whole blood is collected by sterile venipuncture into 60 mL syringes coated with 1.0 mL of sodium-heparin (Upjohn, 1000 U/mL) and diluted 1:1 in Hanks Balanced Salt Solution (Gibco). The erythrocytes are separated from the PBMC's by centrifugation on a Ficoll-Hypaque lymphocyte separation media. The PBMC's are washed three times in Hanks Balanced Salt Solution and then resuspended to a final concentration of 2×10$^6$ cell/mL in RPMI containing 10% fresh autologous human serum, penicillin streptomycin (10 U/mL) and 0.05% DMSO. Lipopolysaccharide (Salmonella type Re545; Sigma Chemicals) is added to the cells to a final concentration of 100 ng/mL. An aliquot (0.1 mL) of the cells is quickly dispensed into each well of a 96 well plate containing 0.1 mL of the test compound, at the appropriate dilution, and are incubated for 24 hours at 37° C. in 5% CO$_2$. At the end of the culture period, cell culture supernatants are assayed for IL-1β, TNF-α, IL-6 and PQE2 production using specific ELISA.

IL-1 Mediated Cytokine Production

Human peripheral blood mononuclear cells are isolated from fresh human blood according to the procedure of Chin and Kostura, *J. Immunol.* 151, 5574–5585 (1993). Whole blood is collected by sterile venipuncture into 60 mL syringes coated with 1.0 mL of sodium-heparin (Upjohn, 1000 U/mL) and diluted 1:1 in Hanks Balanced Salt Solution (Gibco). The erythrocytes are separated from the PBMC's by centrifugation on a Ficoll-Hypaque lymphocyte separation media. The PBMC's are washed three times in Hanks Balanced Salt Solution and then resuspended to a final concentration of 2×10$^6$ cell/mL in RPMI containing 10% fresh autologous human serum, penicillin streptomycin (10 U/mL) and 0.05% DMSO. Endotoxin free recombinant human IL-1b is then added to a final concentration of 50 pMolar. An aliquot (0.1 mL) of the cells is quickly dispensed into each well of a 96 well plate containing 0.1 mL of the compound at the appropriate dilution and incubated for 24 hours at 37° C. in 5% CO$_2$. At the end of the culture period, cell culture supernatants are assayed for TNF-a, IL-6 and PGE2 synthesis using specific ELISA.

Determination of IL-1β, TNF-α, IL-6 and Prostanoid Production from LPS or L-1 Stimulated PBMC's

IL-1β ELISA

Human IL-1β can be detected in cell-culture supernatants or whole blood with the following specific trapping ELISA. 96 well plastic plates (Immulon 4; Dynatech) are coated for 12 hours at 4° C. with 1 mg/mL protein-A affinity chromatography purified mouse anti-human IL-1β monoclonal antibody (purchased as an ascites preparation from LAO Enterprise, Gaithersburg Md.) diluted in Dulbecco's phosphate-buffered saline (—MgCl$_2$, —CaCl$_2$). The plates are washed with PBS-Tween (Kirkegaard and Perry) then blocked with 1% BSA diluent and blocking solution (Kirkegaard and Perry) for 60 minutes at room temperature followed by washing with PBS Tween. IL-1β standards are prepared from purified recombinant IL-1β produced from *E. coli*. The highest concentration begins at 10 ng/mL followed by 11 two-fold serial dilutions. For detection of IL-1β from cell culture supernatants or blood plasma, 10–25 mL of supernatant is added to each test well with 75–90 mL of PBS Tween. Samples are incubated at room temperature for 2 hours then washed 6 times with PBS Tween on an automated plate washer (Dennly). Rabbit anti-human IL-1β polyclonal antisera diluted 1:500 in PBS-Tween is added to the plate and incubated for 1 hour at room temperature followed by six washes with PBS-Tween. Detection of bound rabbit anti-IL-1β IgG is accomplished with Fab' fragments of Goat anti-rabbit IgG-horseradish peroxidase conjugate (Accurate Scientific) diluted 1:10,000 in PBS-Tween. Peroxidase activity was determined using TMB peroxidase substrate kit (Kirkegaard and Perry) with quantitation of color intensity on a 96-well plate Molecular Devices spectrophotometer set to determine absorbance at 450 nM. Samples are evaluated using a standard curve of absorbance versus concentration. Four-parameter logistics analysis generally is used to fit data and obtain concentrations of unknown compounds.

TNF-α ELISA

Immulon 4 (Dynatech) 96-well plastic plates are coated with a 0.5 mg/mL solution of mouse anti-human TNF-a monoclonal antibody. The secondary antibody is a 1:2500 dilution of a rabbit anti-human TNF-α polyclonal serum purchased from Genzyme. All other operations are identical to those described above for IL-1β. The standards are prepared in PBS-Tween+10% FBS or HS. Eleven two-fold dilutions are made beginning at 20 ng/mL TNF-α.

IL-6 ELISA

Levels of secreted human IL-6 are also determined by specific trapping ELISA as described previously in Chin and Kostura, *J. Immunol.* 151, 5574–5585 (1993). (Dynatech) ELISA plates are coated with mouse anti-human IL-6 monoclonal antibody diluted to 0.5 mg/mL in PBS. The secondary antibody, a rabbit anti-human IL-6 polyclonal antiserum, is diluted 1:5000 with PBS-Tween. All other operations are identical to those described above for IL-1β. The standards are prepared in PBS-Tween+10% FBS or HS. Eleven two-fold dilutions are made beginning at 50 ng/mL IL-6.

$PG_2$ Production

Prostaglandin E2 is detected in cell culture supernatants from LPS or IL-1 stimulated PBMC's using a commercially available enzyme immunoassay. The assay purchased from the Cayman Chemical (Catalogue No. 514010) and is run exactly according to the manufacturers instructions.

Interleukin-8 (IL-8)

The present compounds can also be assayed for IL-8 inhibitory activity as discussed below. Primary human umbilical cord endothelial cells (HUVEC) (Cell Systems, Kirkland, Wash.) are maintained in culture medium supplemented with 15% fetal bovine serum and 1% CS-HBGF consisting of aFGF and heparin. The cells are then diluted 20-fold before being plated (250 μl) into gelatin coated 96-well plates. Prior to use, culture medium is replaced with fresh medium (200 μl). Buffer or test compound (25 μl, at appropriate concentrations) is then added to each well in quadruplicate wells and the plates incubated for 6h in a humidified incubator at 37° C. in an atmosphere of 5% $CO_2$. At the end of the incubation period, supernatant is removed and assayed for IL-8 concentration using an IL-8 ELISA kit obtained from R&D Systems (Minneapolis, Minn.). All data is presented as mean value (ng/mL) of multiple samples based on the standard curve. IC50 values where appropriate are generated by non-linear regression analysis.

What is claimed is:

1. A compound of the formula

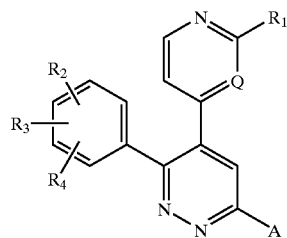

(I)

wherein

A is halogen, phenyl, $S(O)_m$ phenyl, or $NR_5R_6$;

$R_1$ is hydrogen, $NH(C_1-C_6$ alkyl)aryl, $NH(C_1-C_6$ alkyl) or $NH(C_3-C_6$ cycloalkyl), said aryl group being optionally substituted by 1–3 groups selected from halogen, hydroxy, $CF_3$, $NH_2$, and $NO_2$;

$R_2$, $R_3$ and $R_4$ independently represent a member selected from the group consisting of hydrogen, halogen, hydroxy, $CF_3$, $NH_2$, $NO_2$, $C_1-C_6$ alkyl, $C_1-C_6$ alkoxy, $C_3-C_8$ cycloalkyl or phenyl;

$R_5$ and $R_6$ are independently hydrogen, $C_1-C_6$ alkyl, $(C_1-C_6$ alkyl)—O—$(C_1-C_6$ alkyl), $(C_1-C_6$ alkyl) cycloalkyl, $(C_1-C_6$ alkyl) $NR_7R_8$, $C_1-C_6$ alkylphenyl, said phenyl group optionally substituted with 1 to 3 groups selected from $(C_1-C_6$ alkyl) or $(C_1-C_6$ alkoxy); $(C_1-C_6$ alkyl)—NHCOO—$(C_1-C_6$ alkyl), $(C_1-C_6$ alkyl)C≡C, $(C_1-C_6$ alkyl)indole, $(C_1-C_6$ alkyl)

pyridinyl, a pyrrolidinyl or piperidyl group, said groups optionally substituted with $C_1-C_6$ alkyl or benzyl; or $R_5$ and $R_6$ are taken together with the nitrogen atom to form an optionally substituted 4 to 10 membered mono, bicyclic or azabicyclic heterocyclic ring containing at least one N atom, and optionally containing 1–2 additional N atoms and 0–2 O or S atoms, said ring optionally substituted by 1–3 groups selected from $C_1-C_6$alkyl, OH, $O(C_1-C_6$ alkyl), $COO(C_1-C_6$ alkyl), $C_1-C_6$alkyl benzodioxole, $CONR_7R_8$, phenyl, said phenyl group optionally substituted with halogen, $C_1-C_6$alkyl, $C_1-C_6$ alkoxy; $CH(aryl)_2$, said aryl optionally substituted with 1–3 groups selected from $C_1-C_6$alkyl, OH or halogen; $NR_7R_8$;

$R_7$ and $R_8$ are independently hydrogen, $C_1-C_6$ alkyl, $(C_1-C_6$ alkyl)—O—$(C_1-C_6$ alkyl), $C_1-C_6$ alkylaryl, $(C_1-C_6$ alkyl)—NHCOO—$(C_1-C_6$ alkyl), COO—$(C_1-C_6$ alkyl), a pyrrolidinyl or piperidyl group, said groups optionally substituted with $C_1-C_6$ alkyl or $C_1-C_6$ alkylaryl; or $R_7$ and $R_8$ are taken together with the nitrogen atom to form an optionally substituted 4 to 10 membered mono, bicyclic or azabicyclic heterocyclic ring containing at least one N atom, and optionally containing 1–2 additional N atoms and 0–1 O or S atoms, said ring optionally substituted by 1–3 groups selected from $C_1-C_4$alkyl, OH, $O(C_1-C_6$ alkyl), Q is N;

m is 0, 1 or 2;

or a pharmaceutically acceptable addition salt and/or hydrate thereof, or where applicable, a geometric or optical isomer or racemic mixture thereof.

2. The compound in accordance with claim 1 of the formula

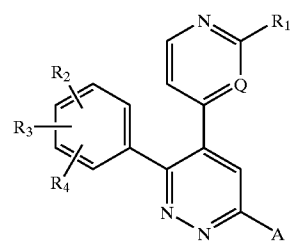

(I)

wherein

A is $NR_5R_6$;

$R_1$ is $NH(C_1-C_6$ alkyl)aryl, said aryl group being optionally substituted by 1–3 groups selected from halogen, hydroxy, $CF_3$, $NH_2$, and $NO_2$;

$R_2$ is $CF_3$;

Q is N;

or a pharmaceutically acceptable addition salt and/or hydrate thereof, or where applicable, a geometric or optical isomer or racemic mixture thereof.

3. A compound as defined in claim 1 of the formula
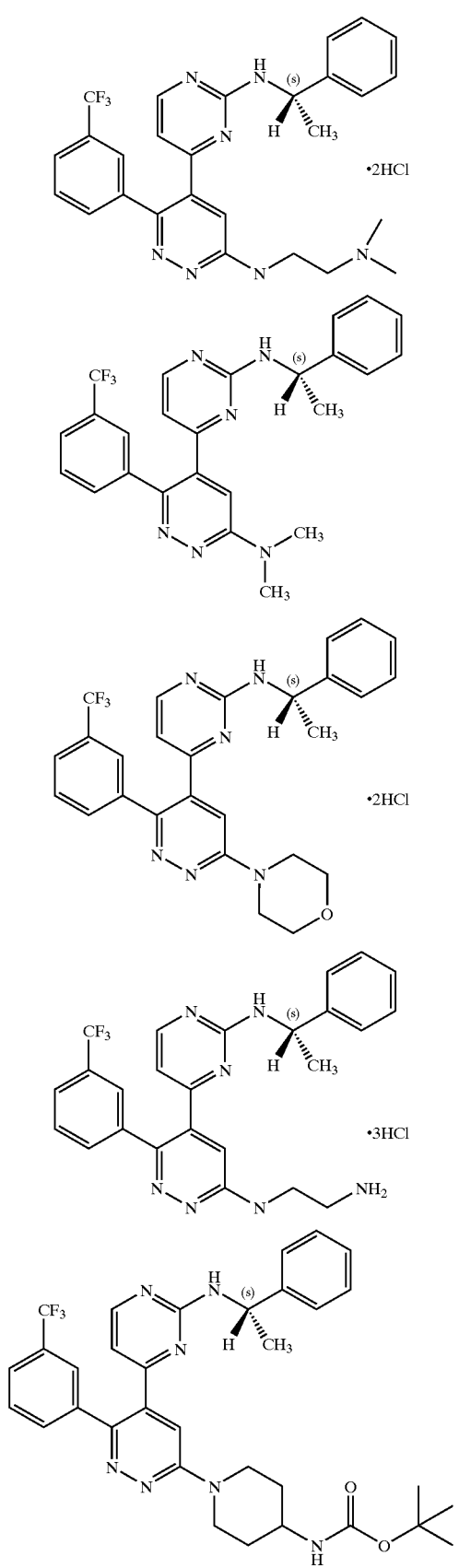
-continued
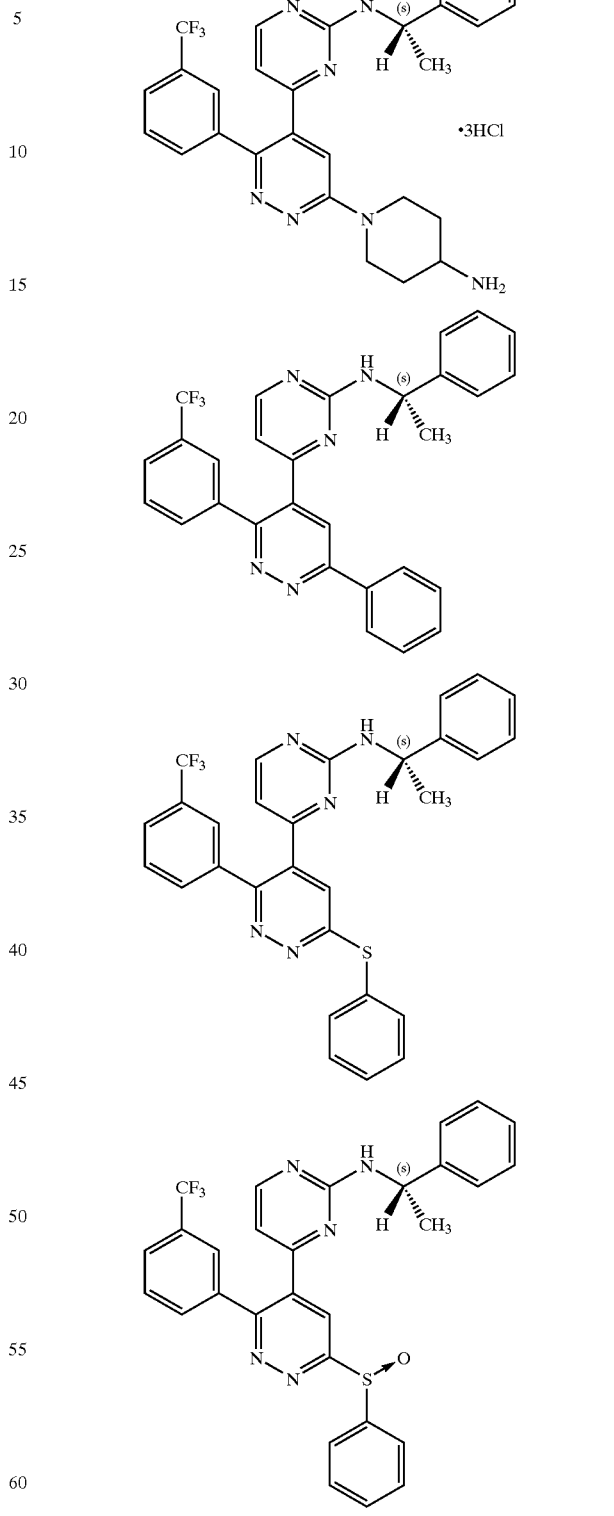
or a pharmaceutically acceptable addition salt and/or hydrate thereof, or where applicable, a geometric or optical isomer or racemic mixture thereof.

4. A compound as defined in claim 1 of the formula

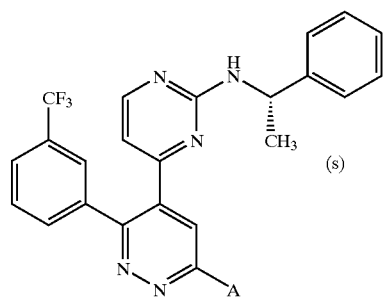

or a pharmaceutically acceptable addition salt and/or hydrate thereof, or where applicable, a geometric or optical isomer or racemic mixture thereof, wherein A is as indicated in the following table:

| Number | A |
|---|---|
| 12 | ⸺NH⸺CH₂CH₂CH₂⸺OCH₃ |
| 13 | ⸺NH⸺CH₂CH₂CH₂⸺OCH₂OCH₃ |
| 14 | ⸺NH⸺(CH₂)₃⸺imidazolyl |
| 15 | ⸺NH⸺(1-benzylpiperidin-4-yl) |
| 16 | ⸺NH⸺CH₂CH₂⸺NH⸺C(O)⸺O⸺C(CH₃)₃ |
| 17 | ⸺NH⸺CH₂⸺(3,4-dimethoxyphenyl) |
| 18 | ⸺(1,4-dioxa-8-azaspiro[4.5]dec-8-yl) |
| 19 | ⸺(imidazol-1-yl) |
| 20 | ⸺(4-methylpiperazin-1-yl) |
| 21 | ⸺(piperazin-1-yl) |
| 22 | ⸺(1,2,3,4-tetrahydroisoquinolin-2-yl) |
| 23 | ⸺(3,5-dimethylpiperidin-1-yl) |
| 24 | ⸺(4-piperidin-1-yl-piperidin-1-yl) |
| 25 | ⸺N(CH₃)⸺(1-methylpyrrolidin-3-yl) |
| 26 | ⸺(4-methyl-1,4-diazepan-1-yl) |
| 27 | ⸺[4-(4-fluorophenyl)piperazin-1-yl] |
| 28 | ⸺(4-methylpiperidin-1-yl) |

-continued

| Number | A |
|---|---|
| 29 | 3-methylpiperidin-1-yl |
| 30 | N-methyl-N-(2-(dimethylamino)ethyl)amino |
| 31 | 4-phenylpiperazin-1-yl |
| 32 | decahydroquinolin-1-yl |
| 33 | piperidin-1-yl |
| 34 | N,N-bis(2-methoxyethyl)amino |
| 35 | N-propyl-N-(cyclopropylmethyl)amino |
| 36 | 4-[(4-chlorophenyl)(phenyl)methyl]piperazin-1-yl |

-continued

| Number | A |
|---|---|
| 37 | 2,6-dimethylmorpholin-4-yl |
| 38 | thiomorpholin-4-yl |
| 39 | 4-phenylpiperidin-1-yl |
| 40 | N-ethyl-N-benzylamino |
| 41 | N,N-dibutylamino |
| 42 | 4-(3,4-dimethylphenyl)piperazin-1-yl |
| 43 | 2-methyl-4-phenylpiperazin-1-yl |
| 44 | 4-(4-methoxyphenyl)-2-methylpiperazin-1-yl |

-continued
| Number | A |
|---|---|
| 45 | 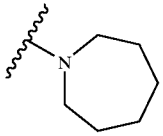 |
| 46 | 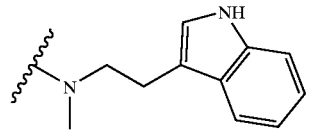 |
| 47 | 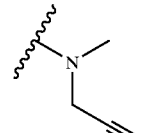 |
| 48 | 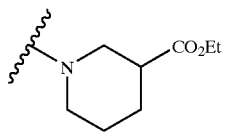 |
| 49 | 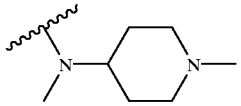 |
| 50 | 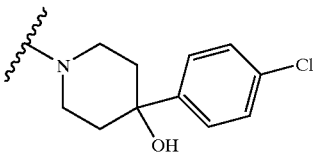 |
| 51 | 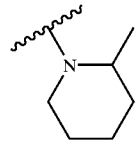 |
| 52 | 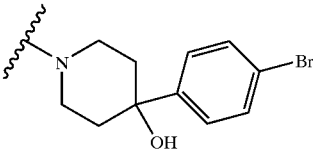 |
| 53 | 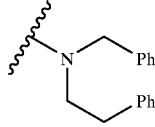 |
| 54 | 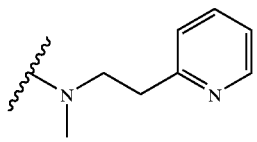 |
-continued
| Number | A |
|---|---|
| 55 | 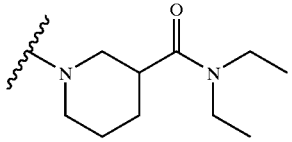 |
| 56 | 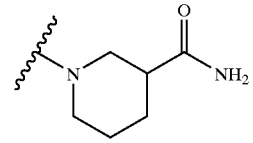 |
| 57 | 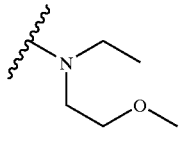 |
| 58 | 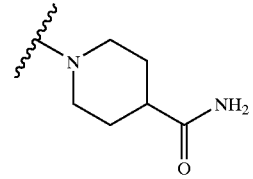 |
| 59 | 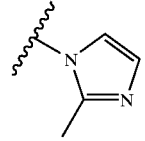 |
| 60 | 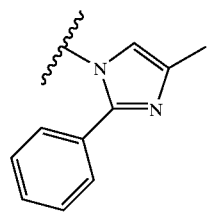 |
| 61 | |
| 62 | |
| 63 | |

-continued

| Number | A |
|---|---|
| 64 | 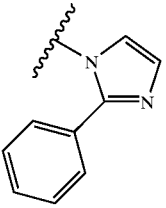 |
| 65 | 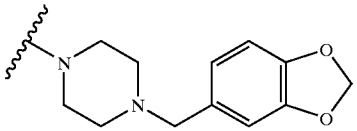 |
| 66 | 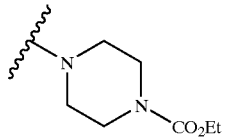 |
| 67 | 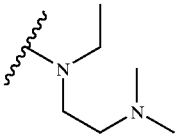 |

-continued

| Number | A |
|---|---|
| 68 | 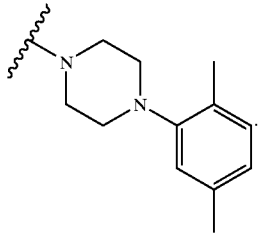 |

5. A pharmaceutical composition which is comprised of a compound in accordance with claim 1 in combination with a pharmaceutically acceptable carrier.

6. A method of treating osteoporosis in a mammalian patient in need of such treatment, comprising administering to said patient an amount of a compound as described in claim 1 which is effective to treat osteoporosis.

7. A method of treating bone resorption in a mammalian patient in need of such treatment, comprising administering to said patient an amount of a compound as described in claim 1 which is effective to treat bone resorption.

8. A method of treating Crohn's disease in a mammalian patient in need of such treatment comprising administering to said patient an amount of a compound as described in claim 1 which is effective to treat Crohn's disease.

9. A process for making a pharmaceutical composition comprising combining the compound of claim 1 and a pharmaceutically acceptable carrier.

* * * * *